(12) United States Patent
Noh et al.

(10) Patent No.: US 9,806,269 B2
(45) Date of Patent: Oct. 31, 2017

(54) DELAYED FLUORESCENCE COMPOUND, AND ORGANIC LIGHT EMITTING DIODE AND DISPLAY DEVICE USING THE SAME

(71) Applicant: LG Display Co., Ltd, Seoul (KR)

(72) Inventors: Hyo-Jin Noh, Paju-si (KR); Kyung-Jin Yoon, Goyang-si (KR); Dae-Wi Yoon, Paju-si (KR); In-Ae Shin, Paju-si (KR); Jun-Yun Kim, Goyang-si (KR)

(73) Assignee: LG Display Co., Ltd., Seoul (KR)

( * ) Notice: Subject to any disclaimer, the term of this patent is extended or adjusted under 35 U.S.C. 154(b) by 146 days.

(21) Appl. No.: 14/954,892

(22) Filed: Nov. 30, 2015

(65) Prior Publication Data
US 2016/0163997 A1 Jun. 9, 2016

(30) Foreign Application Priority Data

Dec. 5, 2014 (KR) ........................ 10-2014-0174199
Sep. 16, 2015 (KR) ........................ 10-2015-0130953

(51) Int. Cl.
| | | |
|---|---|---|
| H01L 51/00 | (2006.01) |
| H01L 51/50 | (2006.01) |
| H01L 27/32 | (2006.01) |
| C07D 209/86 | (2006.01) |
| C07D 495/04 | (2006.01) |
| C09K 11/02 | (2006.01) |
| C09K 11/06 | (2006.01) |
| H01L 51/52 | (2006.01) |

(52) U.S. Cl.
CPC ........ *H01L 51/0071* (2013.01); *C07D 209/86* (2013.01); *C07D 495/04* (2013.01); *C09K 11/02* (2013.01); *C09K 11/06* (2013.01); *H01L 27/3244* (2013.01); *H01L 51/0072* (2013.01); *H01L 51/5004* (2013.01); *H01L 51/5012* (2013.01); *H01L 51/5016* (2013.01); *H01L 51/5028* (2013.01); *C09K 2211/1007* (2013.01); *C09K 2211/1044* (2013.01); *C09K 2211/1051* (2013.01); *C09K 2211/1066* (2013.01); *C09K 2211/1092* (2013.01); *H01L 51/005* (2013.01); *H01L 51/5246* (2013.01); *H01L 2251/5384* (2013.01); *H01L 2251/552* (2013.01)

(58) Field of Classification Search
None
See application file for complete search history.

(56) References Cited

U.S. PATENT DOCUMENTS

| | | |
|---|---|---|
| 2,669,517 A | 2/1954 | Mueller |
| 2014/0145149 A1 | 5/2014 | Lin et al. |
| 2016/0093812 A1 | 3/2016 | Stoessel et al. |

FOREIGN PATENT DOCUMENTS

| | | |
|---|---|---|
| EP | 2687530 A1 | 1/2014 |
| WO | WO 2014/166586 A1 | 10/2014 |

OTHER PUBLICATIONS

Czerwieniec, R. et al., "Radiative Electron Transfer in Planar Donor-Acceptor Quinoxaline Derivatives," Chemical Physics Letters, Aug. 4, 2000, pp. 589-598, vol. 325, No. 5-6.
European Extended Search Report, European Application No. 15197960.6, dated Apr. 21, 2016, 6 pages.
State Intellectual Property Office of the People's Republic of China, First Office Action, Chinese Patent Application No. 201510883588. 4, dated Jul. 14, 2017, thirteen pages.

*Primary Examiner* — Sin Lee
(74) *Attorney, Agent, or Firm* — Fenwick & West LLP

(57) ABSTRACT

Embodiments relate to a delayed fluorescence compound and a display device including the delayed fluorescence compound. The delayed fluorescence compound includes an electron acceptor moiety of benzo[4,5]thieno[2,3-b]quinoxaline and at least one electron donor moiety covalently bonded to the electron acceptor moiety. The at least one electron donor moiety is covalently bonded to a benzene ring of benzo[4,5]thieno[2,3-b]quinoxaline and is selected from carbazole, phenylcarbazole, acridine, and phenylacridine. The effective charge transfer in the delayed fluorescence compound results in improved emitting efficiency of the compound.

19 Claims, 12 Drawing Sheets

Compound 1, HOMO

Compound 1, LUMO

Compound 2, HOMO

Compound 2, LUMO

Compound 3, HOMO

Compound 3, LUMO

Compound 4, HOMO

Compound 4, LUMO

Compound 5, HOMO

Compound 5, LUMO

Compound 6, HOMO

Compound 6, LUMO

Compound 7, HOMO

Compound 7, LUMO

Compound 8, HOMO

Compound 8, LUMO

Compound 9, HOMO

Compound 9, LUMO

Compound 10, HOMO

Compound 10, LUMO

Compound 11, HOMO

Compound 11, LUMO

Compound 12, HOMO

Compound 12, LUMO

Compound 13, HOMO

Compound 13, LUMO

Compound 14, HOMO

Compound 14, LUMO

Compound 15, HOMO

Compound 15, LUMO

Compound 16, HOMO

Compound 16, LUMO

DELAYED FLUORESCENCE COMPOUND, AND ORGANIC LIGHT EMITTING DIODE AND DISPLAY DEVICE USING THE SAME

CROSS-REFERENCE TO RELATED APPLICATIONS

This application claims priority to and the benefit of Republic of Korea Patent Application No. 10-2014-0174199 filed in Republic of Korea on Dec. 5, 2014, and Republic of Korea Patent Application No. 10-2015-0130953 filed in Republic of Korea on Sep. 16, 2015, all of which are hereby incorporated by reference in their entireties.

BACKGROUND OF THE INVENTION

Field of the Invention

The embodiments of the invention relate to an organic light emitting diode (OLED) and more particularly to a delayed fluorescence compound having excellent emitting efficiency and an OLED and a display device using the delayed fluorescence compound.

Discussion of the Related Art

The requirements of the large-sized display device have led to developments in flat panel display devices as an image displaying device. Among the flat panel display devices, the OLED has rapidly developed.

In the OLED, when an electron from a cathode, which serves as an electron-injecting electrode, and a hole from an anode, which serves as a hole-injecting electrode, are injected into an emitting material layer, the electron and the hole are combined and become extinct such that the light is emitted from the OLED. A flexible substrate, for example, a plastic substrate, can be used as a base substrate for the OLED, and the OLED has excellent characteristics of driving voltage, power consumption, and color purity.

The OLED includes a first electrode as an anode on a substrate, a second electrode as a cathode facing the first electrode, and an organic emitting layer therebetween.

To improve the emitting efficiency, the organic emitting layer may include a hole injection layer (HIL), a hole transporting layer (HTL), an emitting material layer (EML), an electron transporting layer (HTL), and an electron injection layer (EIL) sequentially stacked on the first electrode.

The hole is transferred into the EML from the first electrode through the HIL and the HTL, and the electron is transferred into the EML from the second electrode through the EIL and the ETL.

The electron and the hole are combined in the EML to generated excitons, and the excitons are transited from an excited state to a ground state such the light is emitted.

The External quantum efficiency (next) of the emitting material for the EML can be expressed by:

$$\eta_{ext} = \eta_{int} \times r \times \phi \times \eta_{out\text{-}coupling}$$

In the above equation, "$\eta_{int}$" is the internal quantum efficiency, "r" is the charge balance factor, "$\Phi$" is the radiative quantum efficiency, and "$\eta_{out\text{-}coupling}$" is the out-coupling efficiency.

The charge balance factor "r" means a balance between the hole and the electron generating the exciton. Generally, assuming 1:1 matching of the hole and the electrode, the charge balance factor has a value of "1". The radiative quantum efficiency "$\Phi$" is a value regarding an effective emitting efficiency of the emitting material. In the host-dopant system, the radiative quantum efficiency depends on a fluorescent quantum efficiency of the dopant.

The internal quantum efficiency "$\eta_{int}$" is a ratio of the excitons generating the light to the excitons generated by the combination of holes and electrons. In the fluorescent compound, a maximum value of the internal quantum efficiency is 0.25. When the hole and the electron are combined to generate the exciton, a ratio of the singlet excitons to the triplet excitons is 1:3 according to the spin structure. However, in the fluorescent compound, only the singlet excitons excluding the triplet excitons are engaged in the emission.

The out-coupling efficiency "$\eta_{out\text{-}coupling}$" is a ratio of the light emitted from the display device to the light emitted from the EML. When the isotropic compounds are deposited in a thermal evaporation method to form a thin film, the emitting materials are randomly oriented. In this instance, the out-coupling efficiency of the display device may be assumed as 0.2.

Accordingly, the maximum emitting efficiency of the OLED including the fluorescent compound as the emitting material is less than approximately 5%.

To overcome the disadvantage of the emitting efficiency of the fluorescent compound, the phosphorescent compound, where both the singlet excitons and the triplet excitons are engaged in the emission, has been developed for the OLED.

The red and green phosphorescent compounds having a relatively high efficiency are introduced and developed. However, there is no blue phosphorescent compound meeting the requirements in emitting efficiency and reliability.

SUMMARY OF THE INVENTION

Accordingly, embodiments relate to a delayed fluorescence compound and an OLED and a display device using the same that substantially obviate one or more of the problems due to limitations and disadvantages of the related art.

An objective of the embodiment of the invention is to provide a delayed fluorescence compound having high emitting efficiency.

Another objective of the embodiment of the invention is to provide an OLED and a display device having an improved emission efficiency.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the embodiments of the invention, as embodied and broadly described herein, embodiments relate to a delayed fluorescence compound including an electron acceptor moiety of benzo[4,5]thieno[2,3-b]quinoxaline; and an electron donor moiety combined or covalently bonded to a benzene ring of benzo[4,5]thieno[2,3-b]quinoxaline and selected from carbazole, phenylcarbazole, acridine, and phenylacridine.

Embodiments also relate to a delayed fluorescence compound of Formula 1:

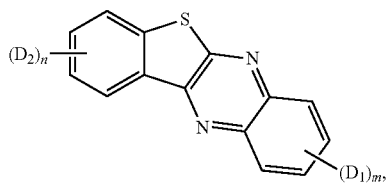

wherein each of m and n is an integer of 0 (zero) to 2, and one of m and n is 0, wherein each of $D_1$ and $D_2$ is independently selected from Formula 2:

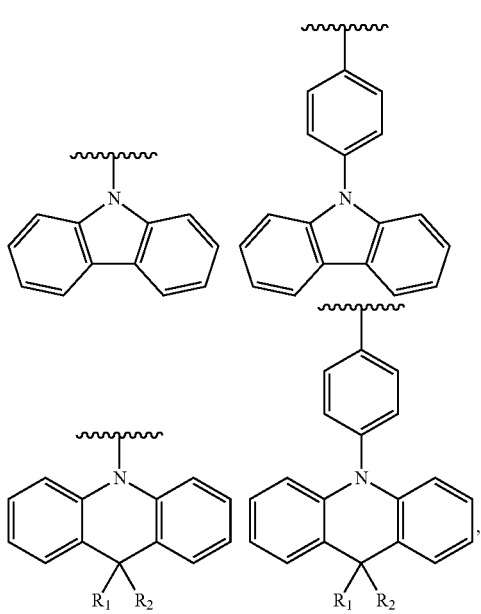

and wherein each of "$R_1$" and "$R_2$" is independently selected from C1~C10 alkyl.

Embodiments also relate to an organic light emitting diode including a first electrode; a second electrode facing the first electrode; and an organic emitting layer between the first and second electrodes and including a delayed fluorescence compound, wherein the delayed fluorescence compound includes an electron acceptor moiety of benzo[4,5]thieno[2,3-b]quinoxaline and an electron donor moiety combined or covalently bonded to a benzene ring of benzo[4,5]thieno[2,3-b]quinoxaline and selected from carbazole, phenylcarbazole, acridine, and phenylacridine.

Embodiments also relate to an organic light emitting diode including a first electrode; a second electrode facing the first electrode; and an organic emitting layer between the first and second electrodes and including a delayed fluorescence compound of Formula 1:

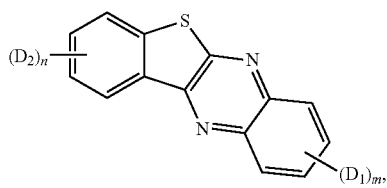

wherein each of m and n is an integer of 0 (zero) to 2, and one of m and n is 0, wherein each of $D_1$ and $D_2$ is independently selected from Formula 2:

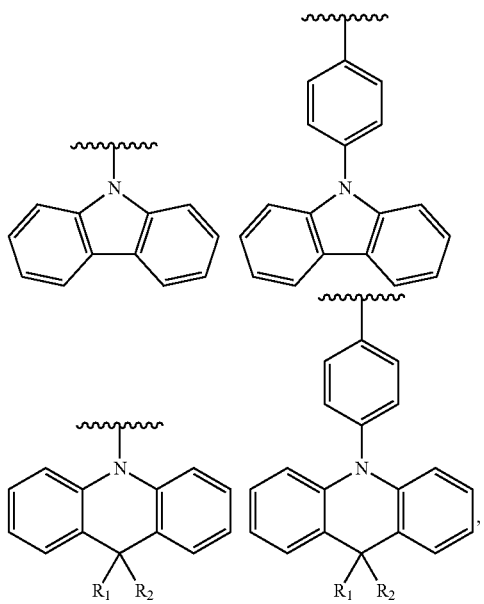

and wherein each of "$R_1$" and "$R_2$" is independently selected from C1~C10 alkyl.

Embodiments also relate to a display device including a substrate; an organic light emitting diode on the substrate and including a first electrode, a second electrode facing the first electrode and an organic emitting layer between the first and second electrodes and including a delayed fluorescence compound; an encapsulation film on the organic light emitting diode; and a cover window on the encapsulation film, wherein the delayed fluorescence compound includes an electron acceptor moiety of benzo[4,5]thieno[2,3-b]quinoxaline and an electron donor moiety combined or covalently bonded to a benzene ring of benzo[4,5]thieno[2,3-b]quinoxaline and selected from carbazole, phenylcarbazole, acridine, and phenylacridine.

Embodiments also relate to a display device including a substrate; an organic light emitting diode on the substrate and including a first electrode, a second electrode facing the first electrode and an organic emitting layer between the first and second electrodes and including a delayed fluorescence compound of Formula 1:

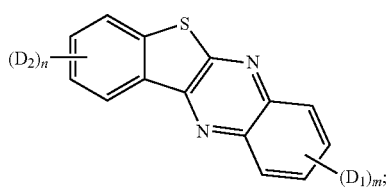

an encapsulation film on the organic light emitting diode; and a cover window on the encapsulation film, wherein each of m and n is an integer of 0 (zero) to 2, and one of m and n is 0, wherein each of $D_1$ and $D_2$ is independently selected from Formula 2:

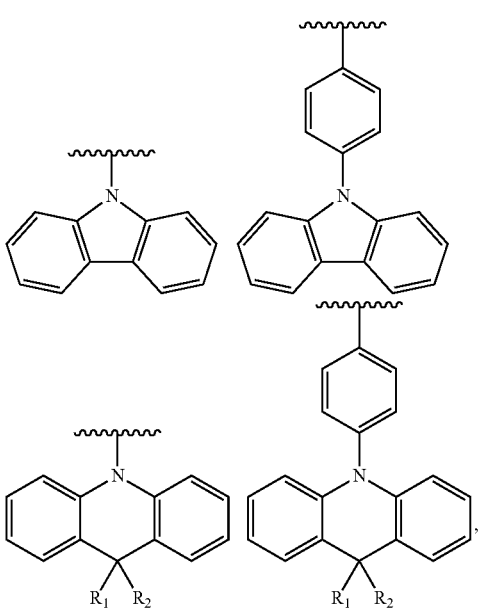

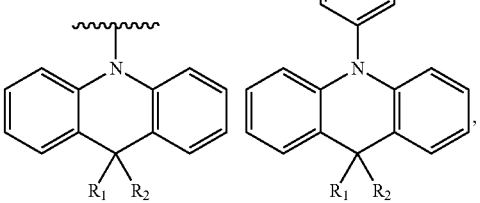

and wherein each of "$R_1$" and "$R_2$" is independently selected from C1~C10 alkyl.

In one embodiment, a difference between a singlet energy of the delayed fluorescence compound and a triplet energy of the delayed fluorescence compound is less than 0.3 eV.

Embodiments also relate to a delayed fluorescence compound including an electron acceptor moiety of benzo[4,5]thieno[2,3-b]quinoxaline and at least one electron donor moiety covalently bonded to a benzene ring of benzo[4,5]thieno[2,3-b]quinoxaline and selected from the group consisting of carbazole, phenylcarbazole, acridine, substituted acridine, phenylacridine, and substituted phenylacridine.

In one embodiment, the delayed fluorescence compound is expressed by Formula 1:

[Formula 1]

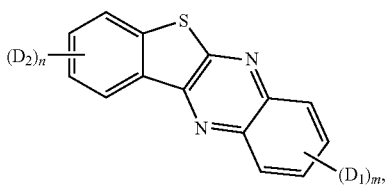

wherein the at least one electron donor moiety corresponds to $(D_1)_m$ and $(D_2)_n$, wherein each of m and n is an integer of 0 (zero) to 2, and one of m and n is 0, and each of $D_1$ and $D_2$ is independently selected from Formula 2:

[Formula 2]

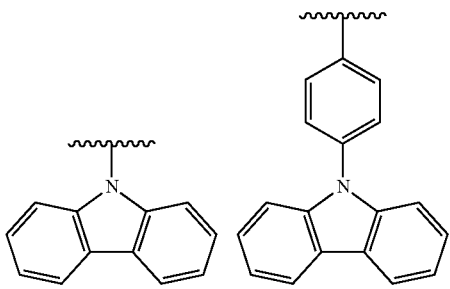

Embodiments also relate to an organic light emitting diode including a first electrode, a second electrode facing the first electrode, and an organic emitting layer between the first electrode and the second electrode, the organic emitting layer including a delayed fluorescence compound. The delayed fluorescence compound includes an electron acceptor moiety of benzo[4,5]thieno[2,3-b]quinoxaline and an electron donor moiety covalently bonded to a benzene ring of benzo[4,5]thieno[2,3-b]quinoxaline. The electron donor moiety is selected from the group consisting of carbazole, phenylcarbazole, acridine, substituted acridine, phenylacridine, and substituted phenylacridine.

In one embodiment, the organic emitting layer includes a hole injection layer (HIL), a hole transporting layer (HTL), an emitting material layer (EML), an electron transporting layer (ETL), and an electron injection layer (EIL). At least one of the HIL, the HTL, the EML, the ETL, and the EIL includes the delayed fluorescence compound.

In one embodiment, a difference between a singlet energy of the delayed fluorescence compound and a triplet energy of the delayed fluorescence compound is less than 0.3 eV.

In one embodiment, the organic emitting layer further includes a host, and the delayed fluorescence compound is used as a dopant.

In one embodiment, a difference between a highest occupied molecular orbital (HOMO) of the host and a HOMO of the dopant or a difference between a lowest unoccupied molecular orbital (LUMO) of the host and a LUMO of the dopant is less than 0.5 eV.

In one embodiment, the organic emitting layer further includes a dopant, and the delayed fluorescence compound is used as a host.

In one embodiment, the organic emitting layer further includes a host and a first dopant, and the delayed fluorescence compound is used as a second dopant, and wherein a triplet energy of the second dopant is smaller than a triplet energy of the host and larger than a triplet energy of the first dopant.

In one embodiment, the delayed fluorescence compound is expressed by Formula 1:

[Formula 1]

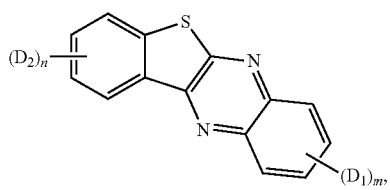

wherein the at least one electron donor moiety corresponds to $(D1)_m$ and $(D2)_n$, each of m and n is an integer of 0 (zero) to 2, one of m and n is 0, and each of $D_1$ and $D_2$ is independently selected from Formula 2:

[Formula 2]

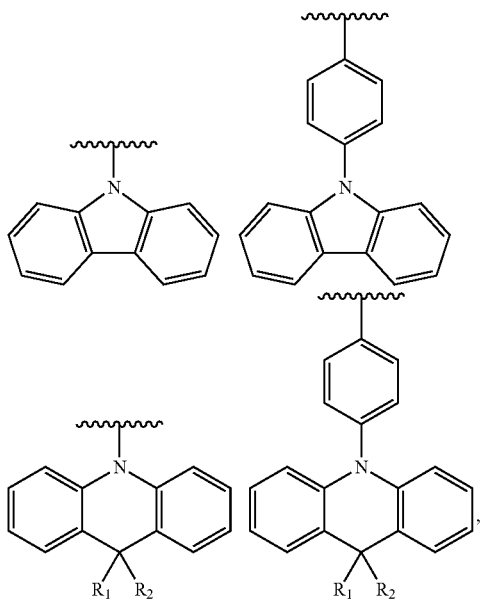

wherein each of "$R_1$" and "$R_2$" is independently selected from C1~C10 alkyl.

Embodiments also relate to a display device including a substrate, an organic light emitting diode on the substrate and including a first electrode, a second electrode facing the first electrode, and an organic emitting layer between the first electrode and the second electrode, the organic emitting layer including a delayed fluorescence compound. The display device further includes an encapsulation film on the organic light emitting diode and a cover window on the encapsulation film. The delayed fluorescence compound includes an electron acceptor moiety of benzo[4,5]thieno[2,3-b]quinoxaline and an electron donor moiety covalently bonded to a benzene ring of benzo[4,5]thieno[2,3-b]quinoxaline. The electron donor moiety is selected from the group consisting of carbazole, phenylcarbazole, acridine, substituted acridine, phenylacridine, and substituted phenylacridine.

In one embodiment, the delayed fluorescence compound is expressed by Formula 1:

[Formula 1]

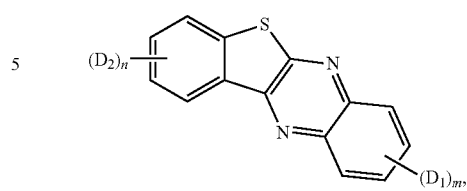

wherein the at least one electron donor moiety corresponds to $(D1)_m$ and $(D2)_n$, each of m and n is an integer of 0 (zero) to 2, one of m and n is 0, and each of $D_1$ and $D_2$ is independently selected from Formula 2:

[Formula 2]

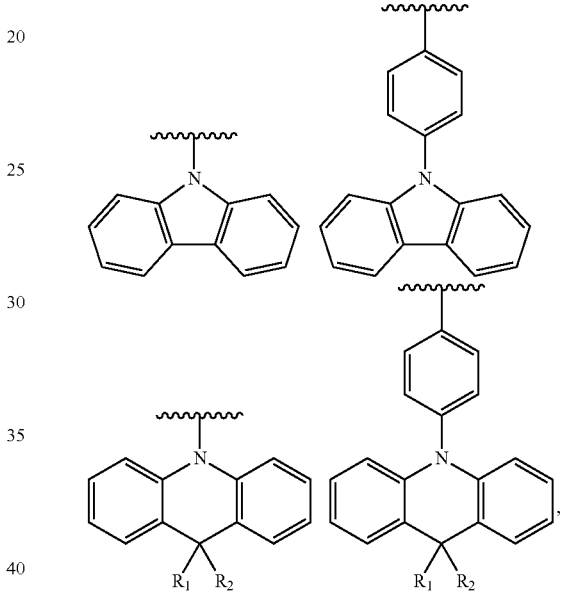

wherein each of "$R_1$" and "$R_2$" is independently selected from C1~C10 alkyl.

In one embodiment, the organic emitting layer includes a hole injection layer (HIL), a hole transporting layer (HTL), an emitting material layer (EML), an electron transporting layer (ETL), and an electron injection layer (EIL). At least one of the HIL, the HTL, the EML, the ETL, and the EIL includes the delayed fluorescence compound.

In one embodiment, a difference between a singlet energy of the delayed fluorescence compound and a triplet energy of the delayed fluorescence compound is less than 0.3 eV.

In one embodiment, the organic emitting layer further includes a host, and the delayed fluorescence compound is used as a dopant.

In one embodiment, a difference between a highest occupied molecular orbital (HOMO) of the host and a HOMO of the dopant or a difference between a lowest unoccupied molecular orbital (LUMO) of the host and a LUMO of the dopant is less than 0.5 eV.

In one embodiment, the organic emitting layer further includes a dopant, and the delayed fluorescence compound is used as a host.

In one embodiment the organic emitting layer further includes a host and a first dopant, and the delayed fluorescence compound is used as a second dopant. A triplet energy of the second dopant is smaller than a triplet energy of the host and larger than a triplet energy of the first dopant.

It is to be understood that both the foregoing general description and the following detailed description are by example and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION OF THE EMBODIMENTS

Figure 1:
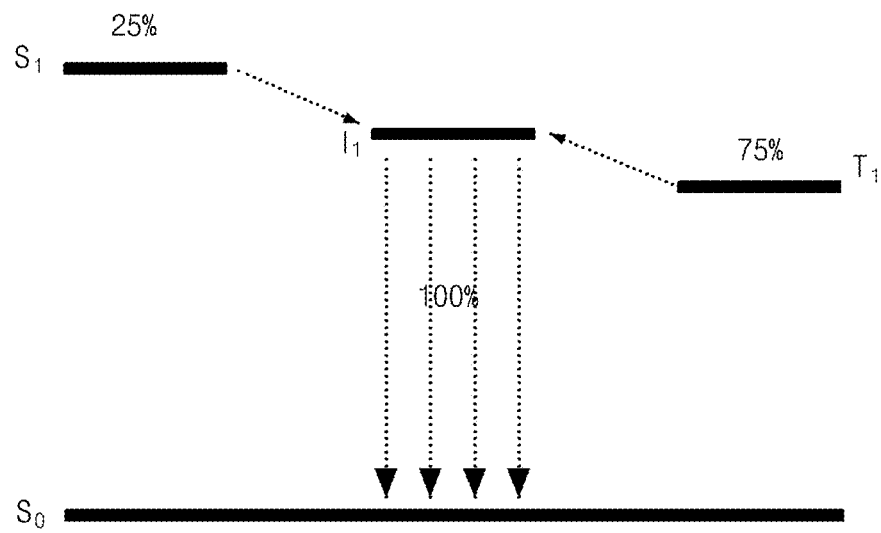
FIG. 1 is a view illustrating an emission mechanism of a delayed fluorescence compound according to the present disclosure.
Figure 2A:
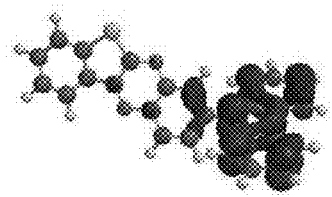
FIGS. 2A and 2B respectively show distribution of HOMO and LUMO of compound 1 of the present disclosure.
Figure 2B:
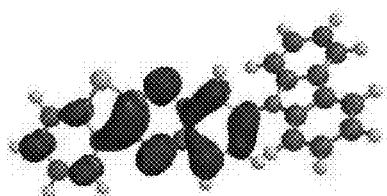
Figure 3A:
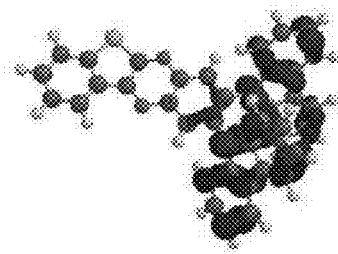
FIGS. 3A and 3B respectively show distribution of HOMO and LUMO of compound 2 of the present disclosure.
Figure 3B:
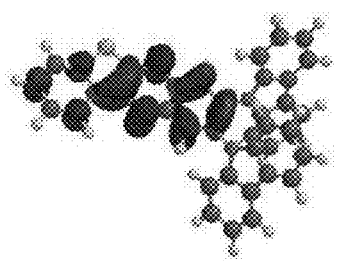
Figure 4A:
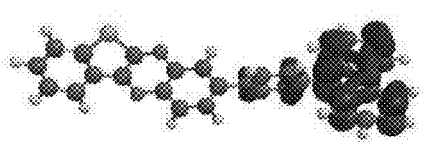
FIGS. 4A and 4B respectively show distribution of HOMO and LUMO of compound 3 of the present disclosure.
Figure 4B:
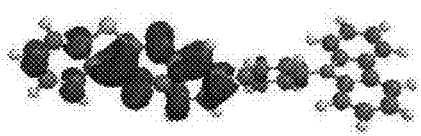
Figure 5A:
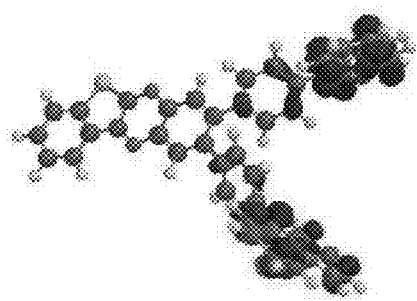
FIGS. 5A and 5B respectively show distribution of HOMO and LUMO of compound 4 of the present disclosure.
Figure 5B:
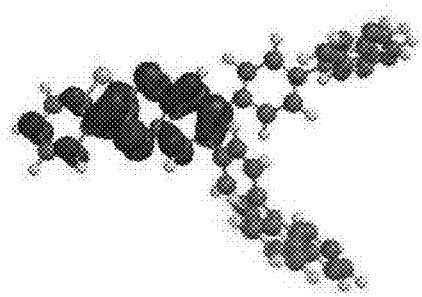
Figure 6A:
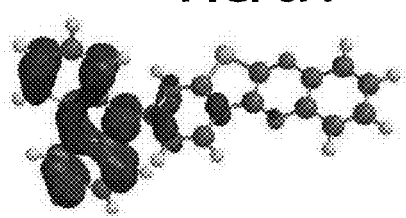
FIGS. 6A and 6B respectively show distribution of HOMO and LUMO of compound 5 of the present disclosure.
Figure 6B:
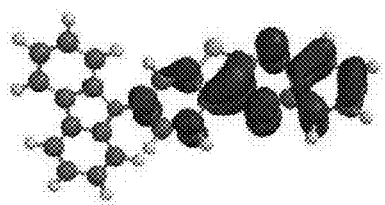
Figure 7A:
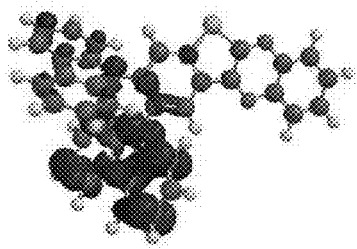
FIGS. 7A and 7B respectively show distribution of HOMO and LUMO of compound 6 of the present disclosure.
Figure 7B:
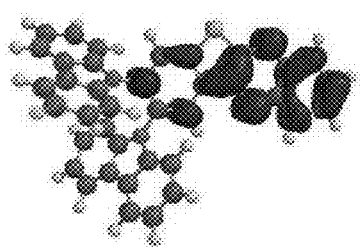
Figure 8A:
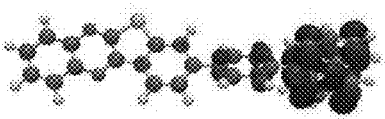
FIGS. 8A and 8B respectively show distribution of HOMO and LUMO of compound 7 of the present disclosure.
Figure 8B:
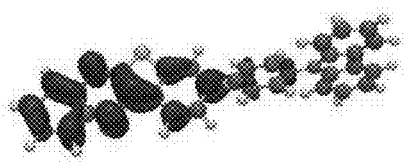
Figure 9A:
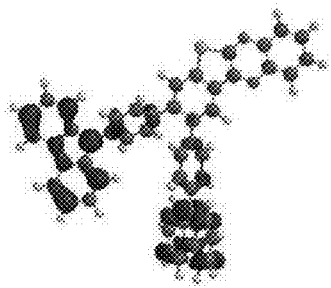
FIGS. 9A and 9B respectively show distribution of HOMO and LUMO of compound 8 of the present disclosure.
Figure 9B:
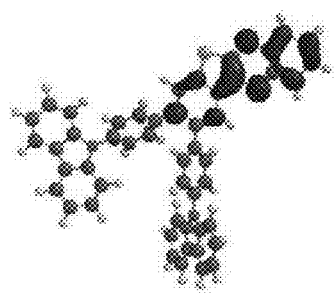
Figure 10A:
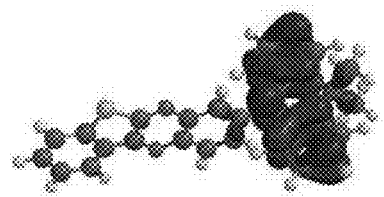
FIGS. 10A and 10B respectively show distribution of HOMO and LUMO of compound 9 of the present disclosure.
Figure 10B:
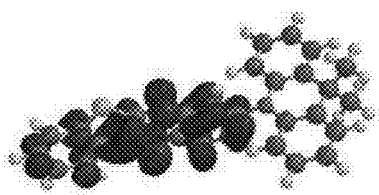
Figure 11A:
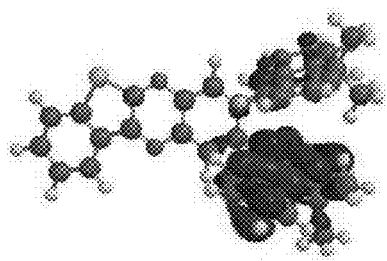
FIGS. 11A and 11B respectively show distribution of HOMO and LUMO of compound 10 of the present disclosure.
Figure 11B:
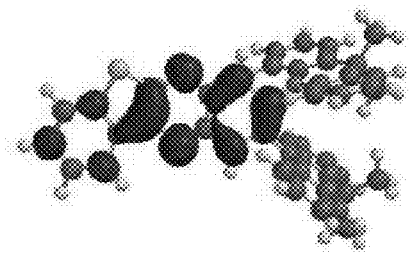
Figure 12A:
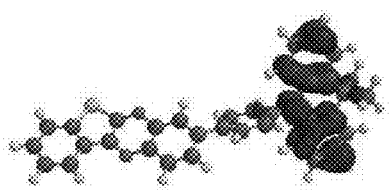
FIGS. 12A and 12B respectively show distribution of HOMO and LUMO of compound 11 of the present disclosure.
Figure 12B:
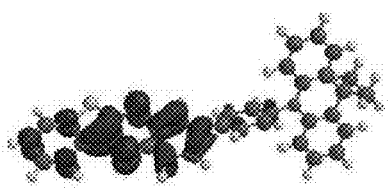
Figure 13A:
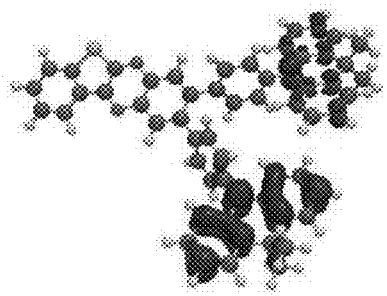
FIGS. 13A and 13B respectively show distribution of HOMO and LUMO of compound 12 of the present disclosure.
Figure 13B:
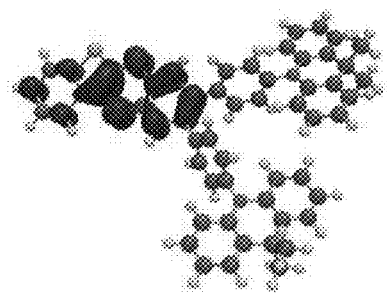
Figure 14A:
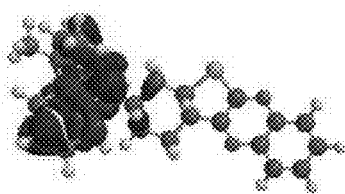
FIGS. 14A and 14B respectively show distribution of HOMO and LUMO of compound 13 of the present disclosure.
Figure 14B:
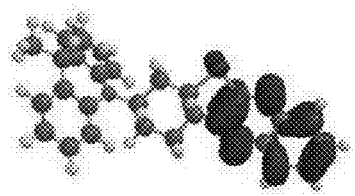
Figure 15A:
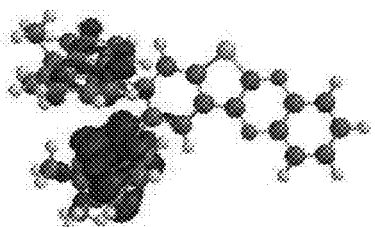
FIGS. 15A and 15B respectively show distribution of HOMO and LUMO of compound 14 of the present disclosure.
Figure 15B:
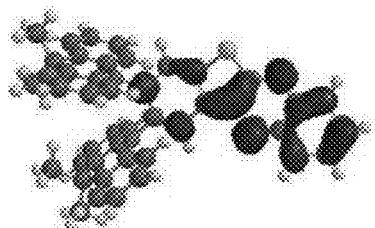
Figure 16A:
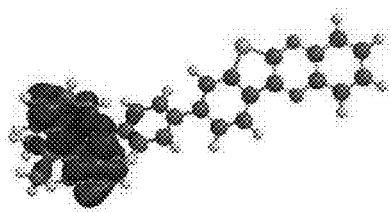
FIGS. 16A and 16B respectively show distribution of HOMO and LUMO of compound 15 of the present disclosure.
Figure 16B:
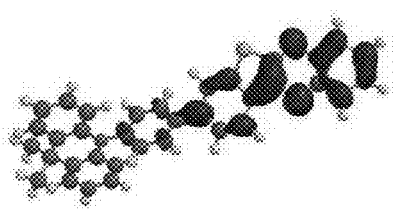
Figure 17A:
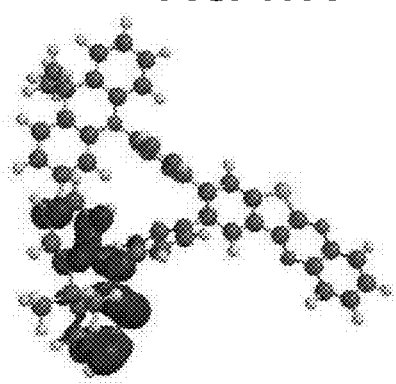
FIGS. 17A and 17B respectively show distribution of HOMO and LUMO of compound 16 of the present disclosure.
Figure 17B:
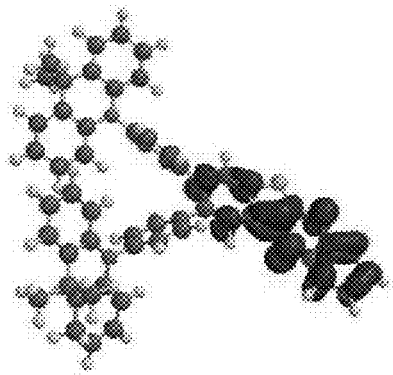

Reference will now be made in detail to example embodiments, examples of which are illustrated in the accompanying drawings.

A delayed fluorescence of the present disclosure has a structure with an electron acceptor moiety of benzo[4,5]thieno[2,3-b]quinoxaline and an electron donor moiety combined or covalently bonded (or linked) to the electron acceptor moiety, given in Formula 1 of following:

[Formula 1]

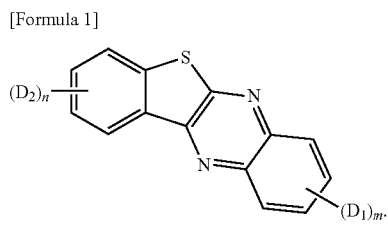

Namely, the electron donor moieties "$D_1$" and "$D_2$" are combined or covalently bonded to a benzene ring of benzo[4,5]thieno[2,3-b]quinoxaline.

In Formula 1, each of "m" and "n" is an integer of 0 (zero) to 2, and one of "m" and "n" is 0. As shown in Formula 2-1, two electron donor moieties "$D_1$" may combine or be covalently bonded to second and third positions of the benzene ring of a quinoxaline part of benzo[4,5]thieno[2,3-b]quinoxaline. As shown in Formula 2-2, one electron donor moiety "D1" may be combined or covalently bonded to positions 6 and 7 of a quinoxaline part of benzo[4,5]thieno[2,3-b]quinoxaline. As shown in Formula 2-3, two electron donor moieties "$D_2$" may be combined or covalently bonded to positions 5 and 6 of a benzothiophene part of benzo[4,5]thieno[2,3-b]quinoxaline. As shown in Formula 2-4, one electron donor moiety "$D_2$" may be combined or covalently bonded to position 6 of a benzothiophene part of benzo[4,5]thieno[2,3-b]quinoxaline.

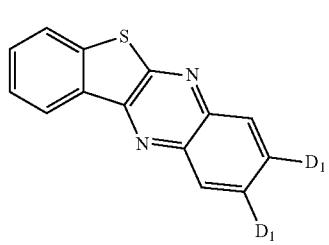

[Formula 2-1]

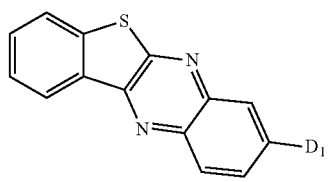

[Formula 2-2]

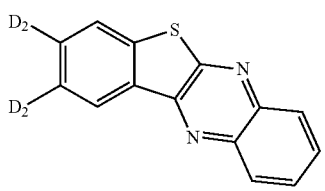

[Formula 2-3]

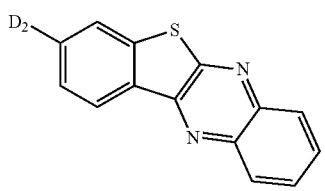

[Formula 2-4]

In Formula 1, each of the electron donor moieties "$D_1$" and "$D_2$" is selected from carbazole, phenylcarbazole, acridine, substituted acridine, phenylacridine, and substituted phenylacridine. Substituted acridine refers to acridine groups having 1 or more substituents selected from the group consisting of alkyl or substituted alkyl. Substituted phenylacridine refers to phenylacridine groups having 1 or more substituents selected from the group consisting of alkyl or substituted alkyl. For example, in Formula 1, each of the electron donor moieties "$D_1$" and "$D_2$" may be selected from Formula 3:

[Formula 3]

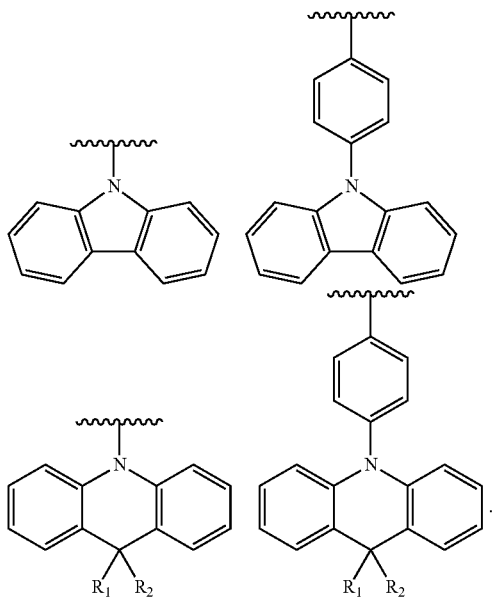

In Formula 3, each of "$R_1$" and "$R_2$" is independently selected from C1 alkyl through C10 alkyl.

In the delayed fluorescence compound, the electron acceptor moiety of benzo[4,5]thieno[2,3-b]quinoxaline and the electron donor moiety are combined or covalently bonded or linked in the molecule such that the charge transfer is easily generated in the molecule and the emitting efficiency is improved. The electron donor moiety may be characterized as a chemical entity that donates or partially transfers electrons to another chemical entity.

Namely, since the delayed fluorescence compound of the present invention includes both of the electron donor moiety and the electron acceptor moiety, the charge is easily transferred in the molecule and the emitting efficiency is improved. In addition, the excitons in the triplet state is used for emission, the emitting efficiency is further improved.

Since benzo[4,5]thieno[2,3-b]quinoxaline as the electron acceptor moiety has a strong electron accepting property and the electron donor moiety is combined or covalently bonded to the electron acceptor moiety, the ratio of the excitons in the triplet state, which are used for the emission, is increased. In addition, since the electron donor moiety of carbazole or acridine and the electron acceptor moiety of benzo[4,5]thieno[2,3-b]quinoxaline form a large dihedral angle, the red shift problem in the emitted light is prevented or minimized.

In the delayed fluorescence compound of the present disclosure, the electron donor moiety and the electron acceptor moiety are combined or linked or covalently bonded in the molecule such that an overlap between highest occupied molecular orbital (HOMO) and lowest unoccupied molecular orbital (LUMO) is reduced. As a result, a charge transfer complex is generated, and the emitting efficiency of the delayed fluorescence compound is improved.

Referring to FIG. 1, which is a view illustrating an emission mechanism of a delayed fluorescence compound according to the present disclosure, the triplet excitons as well as the singlet excitons are engaged in the emission such that the emitting efficiency is improved.

Namely, the triplet exciton is activated by a field, and the triplet exciton and the singlet exciton are transferred into an intermediated state "$I_1$" and transited into a ground state "So" to emit light. In other words, the singlet state "$S_1$" and the triplet state "$T_1$" are transited into the intermediated state "$I_1$" ($S_1 \rightarrow I_1 \leftarrow T_1$), and the singlet exciton and the triplet exciton in the intermediated state "$I_1$" are engaged in the emission such that the emitting efficiency is improved. The compound having the above emission mechanism may be referred to as a field activated delayed fluorescence (FADF) compound.

In the related art fluorescence compound, since the HOMO and the LUMO are dispersed throughout an entirety of the molecule, the interconversion of the HOMO and the LUMO is impossible. (Selection Rule)

However, in the FADF compound, since the overlap between the HOMO and the LUMO in the molecule is relatively small, the interaction between the HOMO and the LUMO is small. Accordingly, changes of the spin state of one electron do not affect other electrons, and a new charge transfer band, which does not comply with the Selection Rule, is generated.

Moreover, since the electron donor moiety and the electron acceptor moiety are spatially spaced apart from each other in the molecule, the dipole moment is generated in a polarized state. In the polarized state dipole moment, the interaction between the HOMO and the LUMO is further reduced such that the emission mechanism does not comply with the Selection Rule. Accordingly, in the FADF compound, the transition from the triplet state "$T_1$" and the singlet state "$S_1$" into the intermediated state "$I_1$" can be generated such that the triplet exciton can be engaged in the emission.

When the OLED is driven, the intersystem transition (intersystem crossing) from 25% singlet state "$S_1$" excitons and 75% triplet state "$T_1$" excitons to the intermediated state "$I_1$" is generated, and the singlet and triplet excitons in the intermediated state "$I_1$" are transited into the ground state to emit light. As a result, the FADF compound has the theoretic quantum efficiency of 100%.

For example, the delayed fluorescence compound in Formula 1 may be one of compounds in Formula 4.

[Formula 4]

compound 1
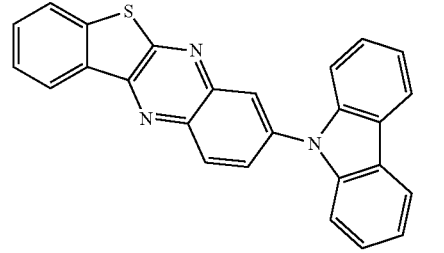

compound 2
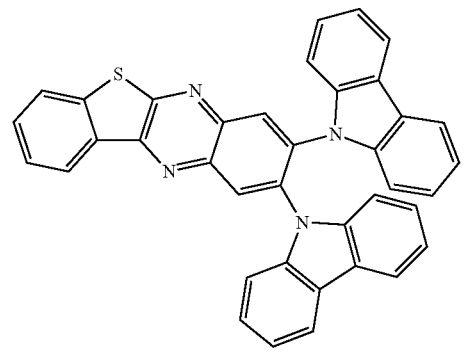

compound 3
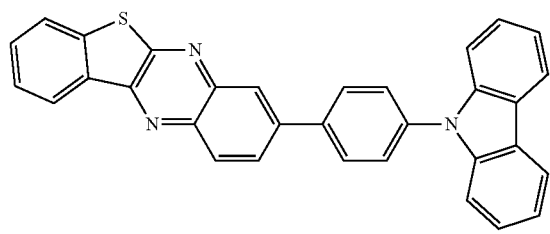

compound 4
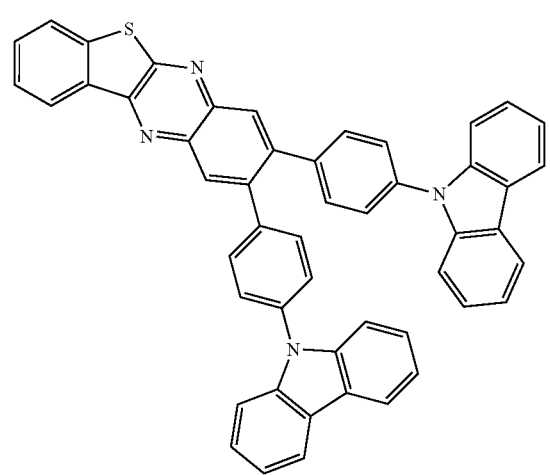

compound 5
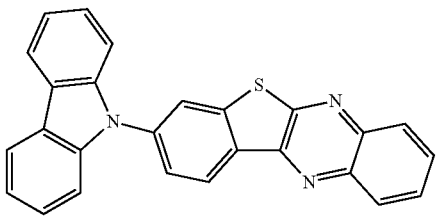

compound 6
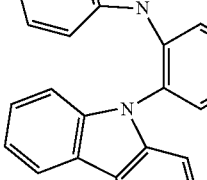

compound 7
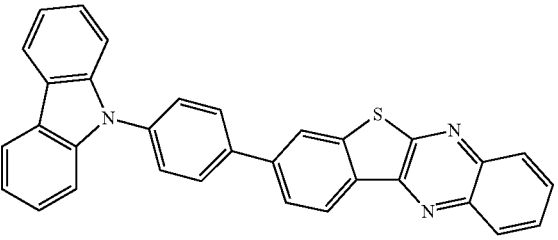

compound 8
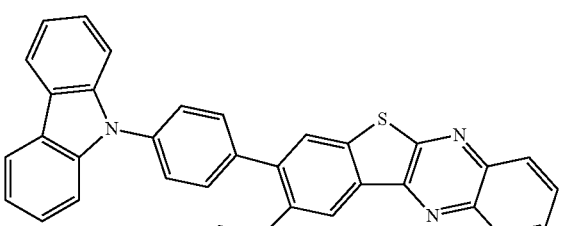

compound 8
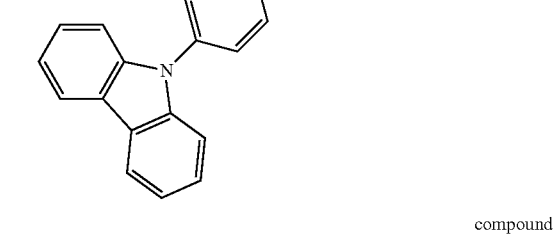

compound 9
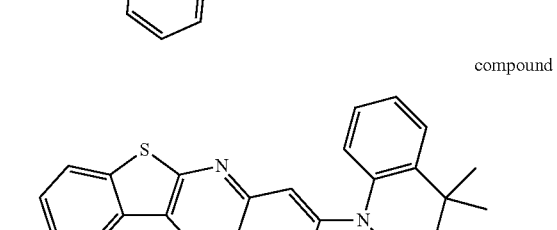

compound 10

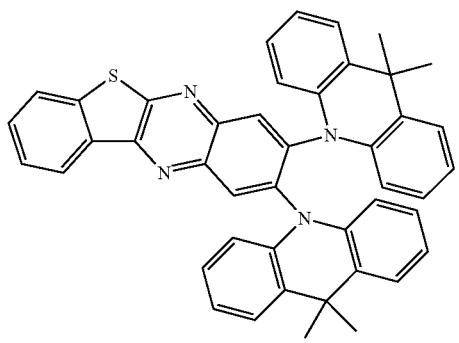

compound 14

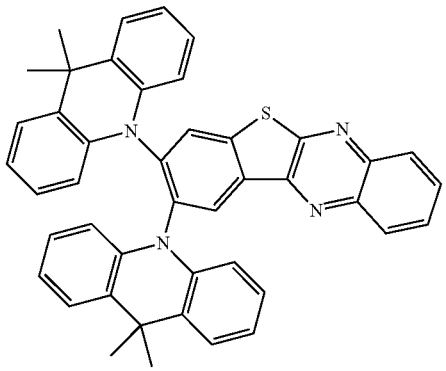

compound 11

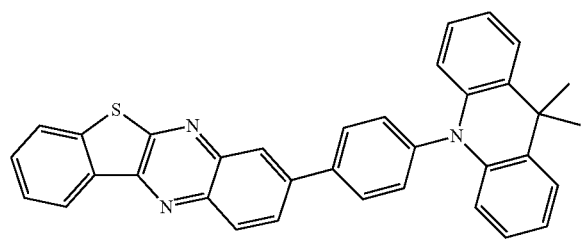

compound 15

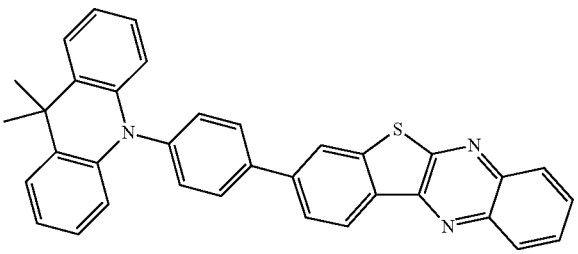

compound 12

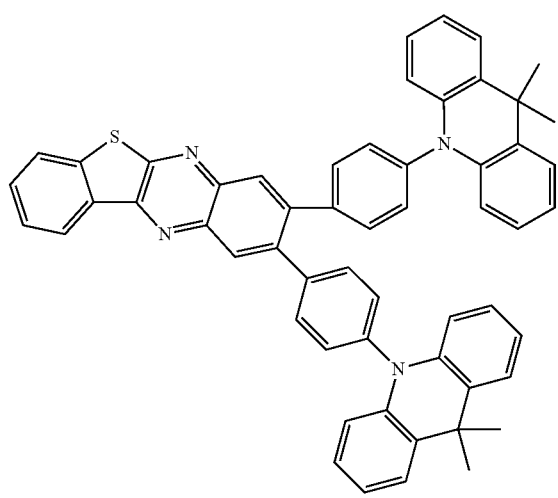

compound 16

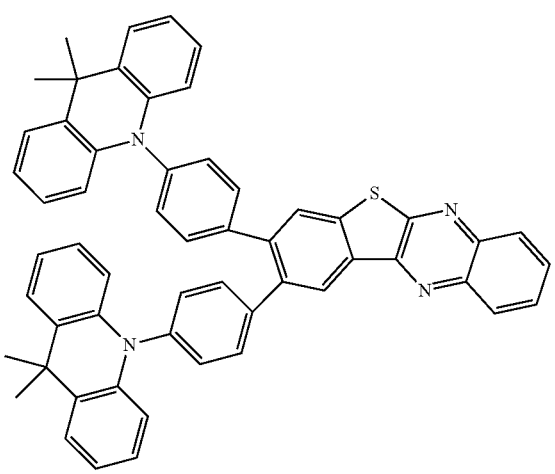

compound 13

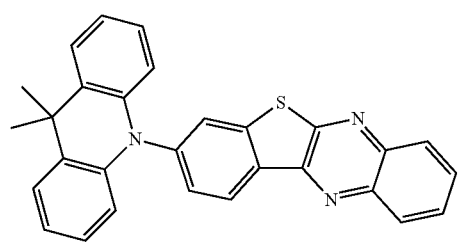

The delayed fluorescence compound of the present disclosure includes the electron acceptor moiety of benzo[4,5]thieno[2,3-b]quinoxaline and the electron donor moiety of carbazole, phenylcarbazole, acridine, or phenylacridine such that the emitting efficiency is increased and the color purity is improved.

The HOMO, the LUMO, and the energy band gap of the compounds 1 to 16 are listed in Table 1, and the distribution of the HOMO and the LUMO of the compounds 1 to 16 are shown in FIGS. 2A to 17B.

TABLE 1

|      | HOMO  | LUMO  | Band gap |
|------|-------|-------|----------|
| Com1 | −5.45 | −1.62 | 3.83     |
| Com2 | −5.45 | −1.65 | 3.80     |
| Com3 | −5.37 | −1.55 | 3.82     |
| Com4 | −5.36 | −1.53 | 3.83     |
| Com5 | −5.49 | −1.42 | 4.07     |

TABLE 1-continued

|      | HOMO  | LUMO  | Band gap |
|------|-------|-------|----------|
| Com6 | −5.43 | −1.52 | 3.91 |
| Com7 | −5.40 | −1.35 | 4.05 |
| Com8 | −5.36 | −1.54 | 3.82 |
| Com9 | −5.35 | −1.63 | 3.72 |
| Com10 | −5.38 | −1.67 | 3.71 |
| Com11 | −5.29 | −1.52 | 3.77 |
| Com12 | −5.27 | −1.50 | 3.77 |
| Com13 | −5.41 | −1.44 | 3.97 |
| Com14 | −5.39 | −1.54 | 3.85 |
| Com15 | −5.35 | −1.30 | 4.05 |
| Com16 | −5.39 | −1.51 | 3.88 |

As shown in Table 1 and FIGS. 2A to 17B, the delayed fluorescence compound of the present disclosure has the energy band gap above 3.5 eV, and the separation of the HOMO and the LUMO is easily generated. Accordingly, in the delayed fluorescence compound as the FADF compound, the excitons in the triplet state are engaged in the emission, and the deep blue light is provided.

Synthesis

1. Synthesis of Compound 1

(1) Compound C

[Reaction Formula 1-1]

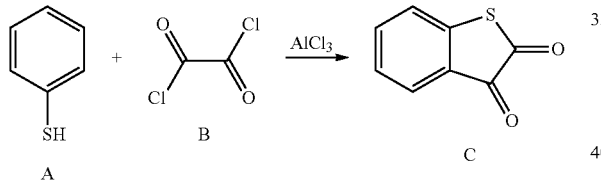

In the $N_2$ gas purging system, compound A (1.0 equivalent) was put into and dissolved in diethyl ether, and compound B (1.2 equivalent) dissolved in methylene chloride (MC) was slowly dropped into the mixture under a temperature of 0° C. The mixture was stirred for 3 hours under room temperature, and aluminum chloride (3 equivalent) was slowly dropped into the mixture under a temperature of 0° C. After stirring the mixture for 12 hours, HCl solution (1M) was slowly put into the mixture to complete the reaction and to be extracted. The resultant was short-columned using hexane such that compound C of white solid was obtained.

(2) Compound E

[Reaction Formula 1-2]

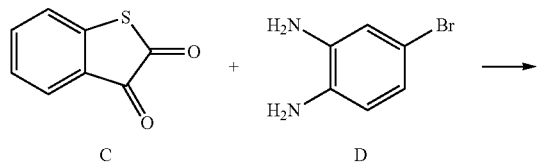

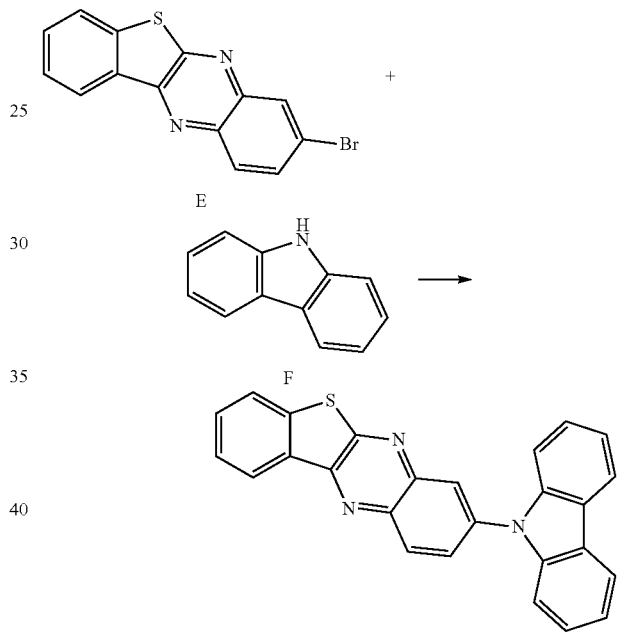

In the $N_2$ gas purging system, compound C (1.0 equivalent), compound D (1.5 equivalent) were put into acetic acid, and the mixture was stirred under a temperature of 90° C. 16 hours after, water was added to complete the reaction and to be extracted. By precipitating the resultant using MC and hexane, compound E of white solid was obtained.

(3) Compound 1

[Reaction Formula 1-3]

In the $N_2$ gas purging system, compound E (1.0 equivalent), compound F (1.2 equivalent), CuI (1.0 equivalent), diaminocyclohexane (3.5 equivalent), and potassium phosphate (4.0 equivalent) were put into 1,4-dioxane, and the mixture was stirred in an oil bath under a temperature of 90° C. 14 hours after, water was added into the mixture to be extracted, and the resultant was columned using the developing solvent of hexane and MC (9:1) such that compound 1 of white solid was obtained.

2. Synthesis of Compound 2

(1) Compound H

[Reaction Formula 2-1]

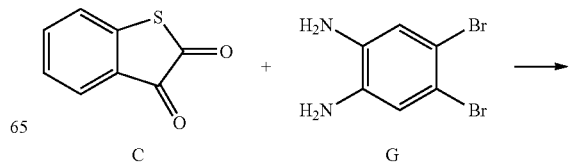

-continued

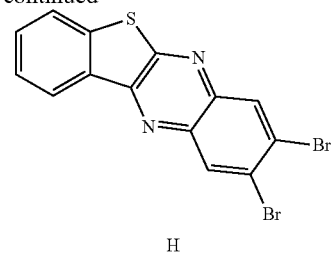

H

In the N₂ gas purging system, compound C (1.0 equivalent), compound G (1.5 equivalent) were put into acetic acid, and the mixture was stirred under a temperature of 90° C. 16 hours after, water was added to complete the reaction and to be extracted. By precipitating the resultant using MC and hexane, compound H of white solid was obtained.

(2) Compound 2

[Reaction Formula 2-2]

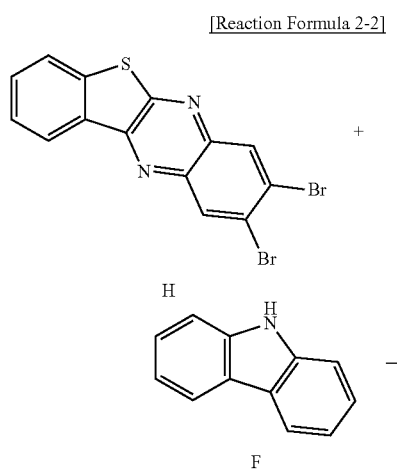

In the N₂ gas purging system, compound H (1.0 equivalent), compound F (2.3 equivalent), CuI (1.0 equivalent), diaminocyclohexane (3.5 equivalent), and potassium phosphate (4.0 equivalent) were put into 1,4-dioxane, and the mixture was stirred in an oil bath under a temperature of 90° C. 18 hours after, water was added into the mixture to be extracted, and the resultant was columned using the developing solvent of hexane and MC (3:1) such that compound 2 of white solid was obtained.

3. Synthesis of Compound 3

[Reaction Formula 3]

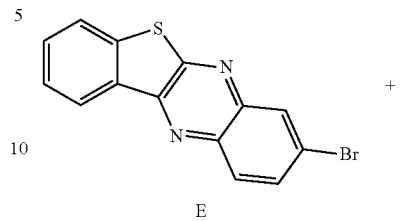

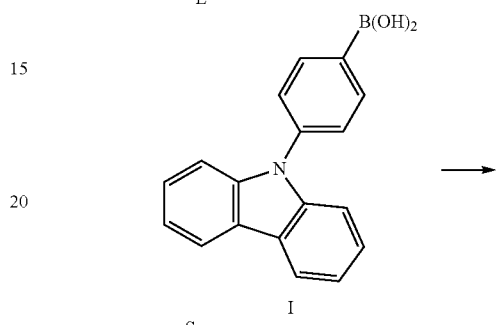

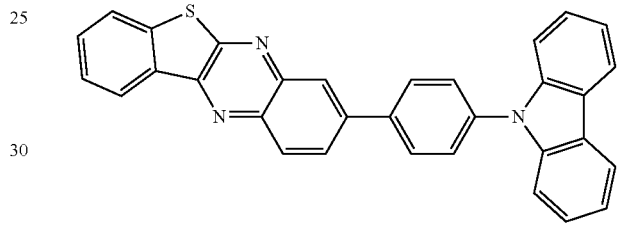

In the N₂ gas purging system, compound E (1.0 equivalent), compound I (1.3 equivalent), Pd(0) (0.05 equivalent), and potassium carbonate (4.0 equivalent) were put into toluene, and the mixture was stirred in an oil bath under a temperature of 80° C. 12 hours after, water was added into the mixture to be extracted, and the resultant was columned using the developing solvent of hexane and MC (4:1) such that compound 3 of white solid was obtained.

4. Synthesis of Compound 4

[Reaction Formula 4]

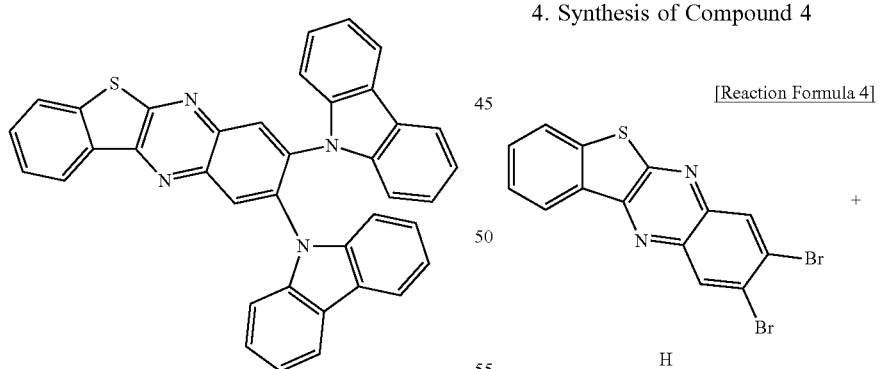

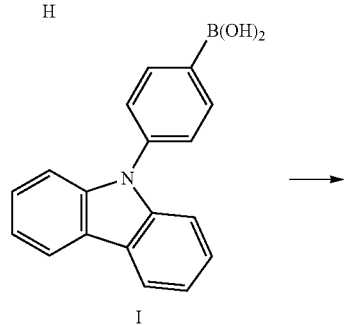

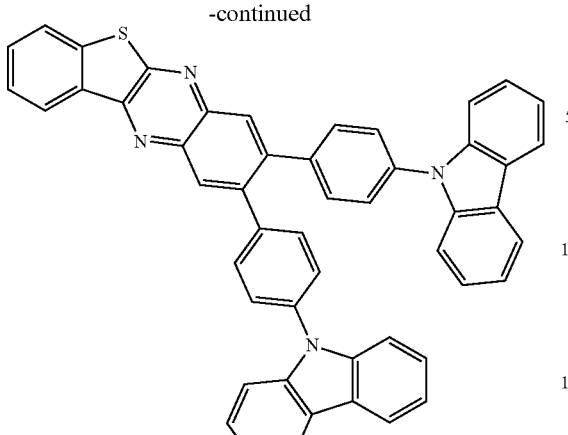

In the N₂ gas purging system, compound H (1.0 equivalent), compound I (2.3 equivalent), Pd(0) (0.05 equivalent), and potassium carbonate (4.0 equivalent) were put into toluene, and the mixture was stirred in an oil bath under a temperature of 80° C. 16 hours after, water was added into the mixture to be extracted, and the resultant was columned using the developing solvent of hexane and ethylene acetate (EA) (4:1) such that compound 4 of white solid was obtained.

5. Synthesis of Compound 5

(1) compound K

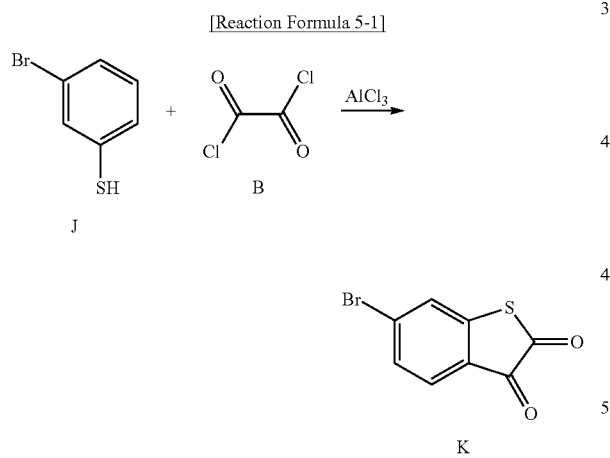

In the N₂ gas purging system, compound J (1.0 equivalent) was put into and dissolved in diethyl ether, and compound B (1.2 equivalent) dissolved in methylene chloride (MC) was slowly dropped into the mixture under a temperature of 0° C. The mixture was stirred for 3 hours under room temperature, and aluminum chloride (3 equivalent) was slowly dropped into the mixture under a temperature of 0° C. After stirring the mixture for 12 hours, HCl solution (1M) was slowly put into the mixture to complete the reaction and to be extracted. The resultant was short-columned using hexane such that compound K of white solid was obtained.

(2) Compound M

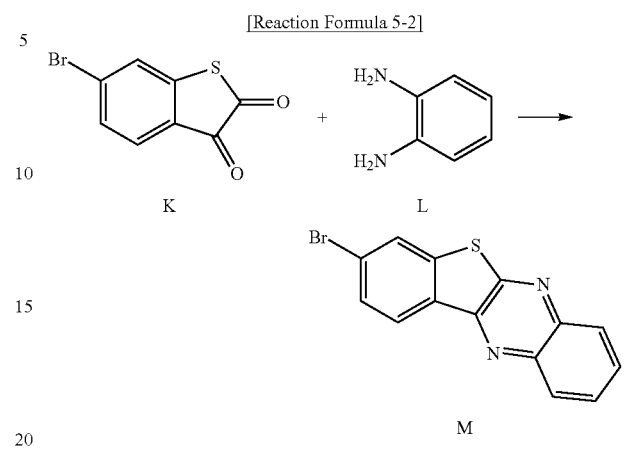

In the N₂ gas purging system, compound K (1.0 equivalent), compound L (1.5 equivalent) were put into acetic acid, and the mixture was stirred under a temperature of 90° C. 16 hours after, water was added to complete the reaction and to be extracted. By precipitating the resultant using MC and hexane, compound M of white solid was obtained.

(3) Compound 5

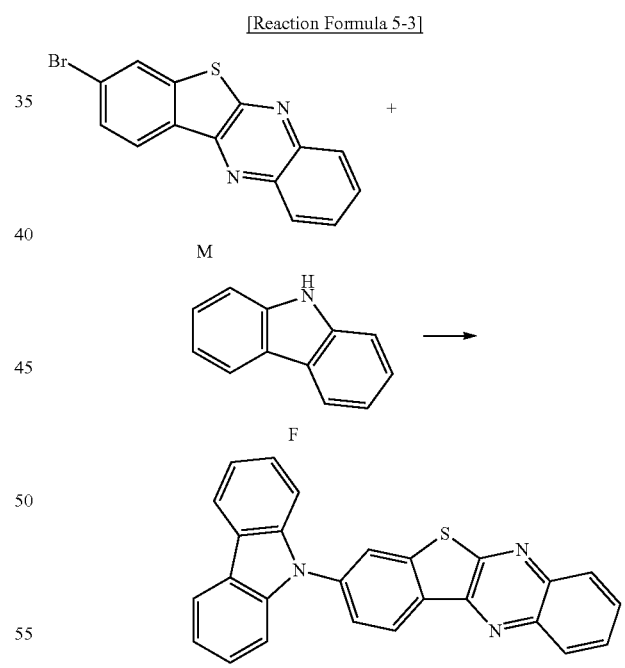

In the N₂ gas purging system, compound M (1.0 equivalent), compound F (1.2 equivalent), CuI (1.0 equivalent), diaminocyclohexane (3.5 equivalent), and potassium phosphate (4.0 equivalent) were put into 1,4-dioxane, and the mixture was stirred in an oil bath under a temperature of 90° C. 12 hours after, water was added into the mixture to be extracted, and the resultant was columned using the developing solvent of hexane and MC (5:1) such that compound 5 of white solid was obtained.

6. Synthesis of Compound 6

(1) Compound O

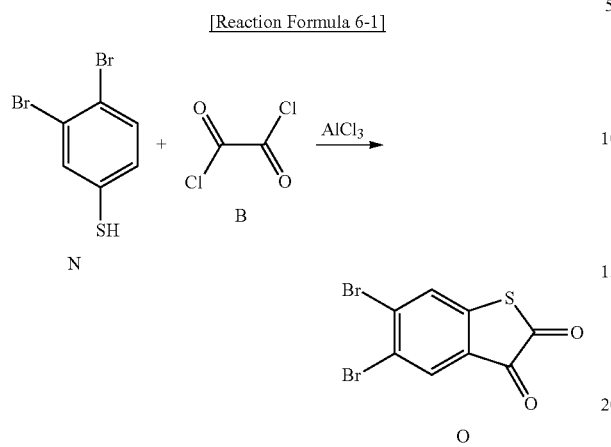

In the N₂ gas purging system, compound N (1.0 equivalent) was put into and dissolved in diethyl ether, and compound B (1.2 equivalent) dissolved in methylene chloride (MC) was slowly dropped into the mixture under a temperature of 0° C. The mixture was stirred for 3 hours under room temperature, and aluminum chloride (3 equivalent) was slowly dropped into the mixture under a temperature of 0° C. After stirring the mixture for 12 hours, HCl solution (1M) was slowly put into the mixture to complete the reaction and to be extracted. The resultant was short-columned using hexane such that compound O of white solid was obtained.

(2) Compound P

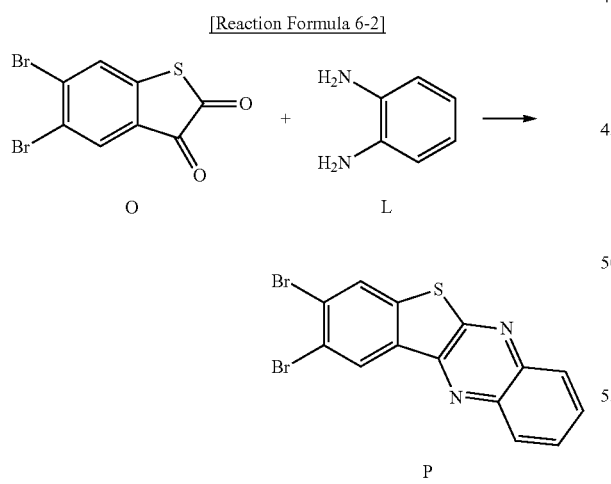

In the N₂ gas purging system, compound O (1.0 equivalent), compound L (1.5 equivalent) were put into acetic acid, and the mixture was stirred under a temperature of 90° C. 16 hours after, water was added to complete the reaction and to be extracted. By precipitating the resultant using MC and hexane, compound P of white solid was obtained.

(3) Compound 6

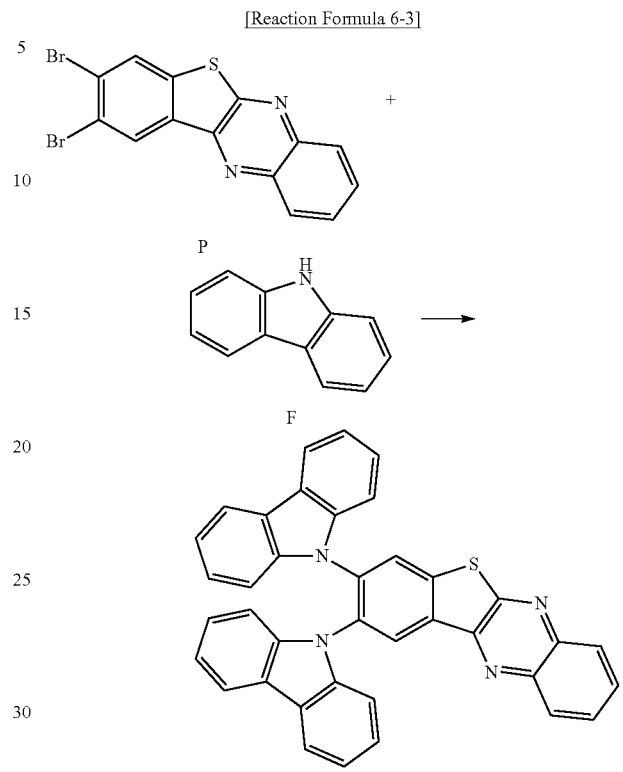

In the N₂ gas purging system, compound P (1.0 equivalent), compound F (2.3 equivalent), CuI (1.0 equivalent), diaminocyclohexane (3.5 equivalent), and potassium phosphate (4.0 equivalent) were put into 1,4-dioxane, and the mixture was stirred in an oil bath under a temperature of 90° C. 18 hours after, water was added into the mixture to be extracted, and the resultant was columned using the developing solvent of hexane and MC (3:2) such that compound 6 of white solid was obtained.

7. Synthesis of Compound 7

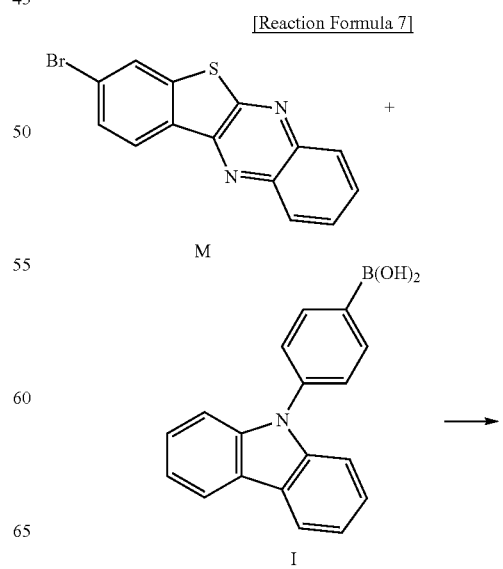

-continued

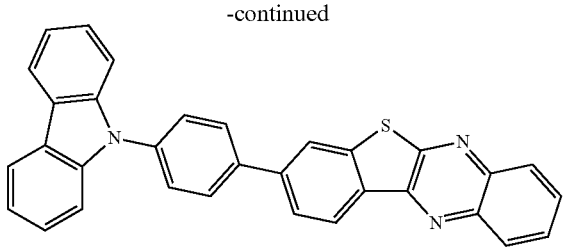

In the N₂ gas purging system, compound M (1.0 equivalent), compound I (1.3 equivalent), Pd(0) (0.05 equivalent), and potassium carbonate (4.0 equivalent) were put into toluene, and the mixture was stirred in an oil bath under a temperature of 80° C. 13 hours after, water was added into the mixture to be extracted, and the resultant was columned using the developing solvent of hexane and MC (4:1) such that compound 7 of white solid was obtained.

8. Synthesis of Compound 8

[Reaction Formula 8]

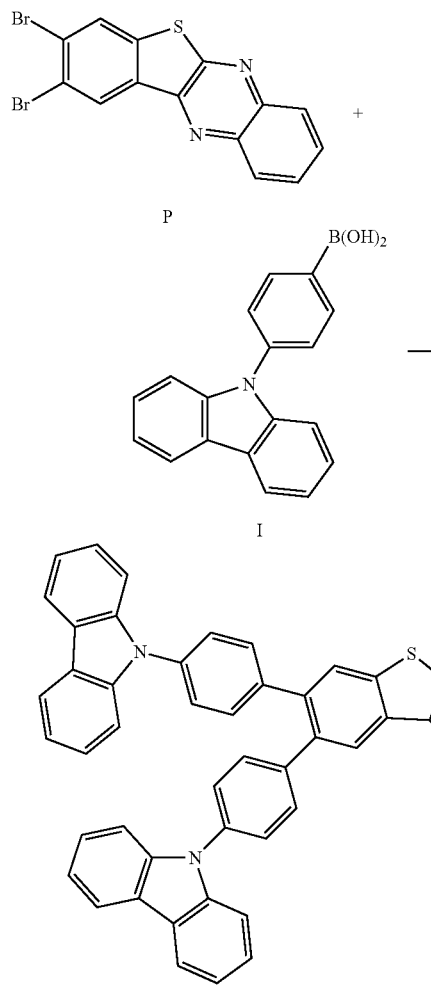

In the N₂ gas purging system, compound P (1.0 equivalent), compound I (2.3 equivalent), Pd(0) (0.05 equivalent), and potassium carbonate (4.0 equivalent) were put into toluene, and the mixture was stirred in an oil bath under a temperature of 80° C. 20 hours after, water was added into the mixture to be extracted, and the resultant was columned using the developing solvent of hexane and ethylene acetate (EA) (3:1) such that compound 8 of white solid was obtained.

9. Synthesis of Compound 9

(1) Compound R

[Reaction Formula 9-1]

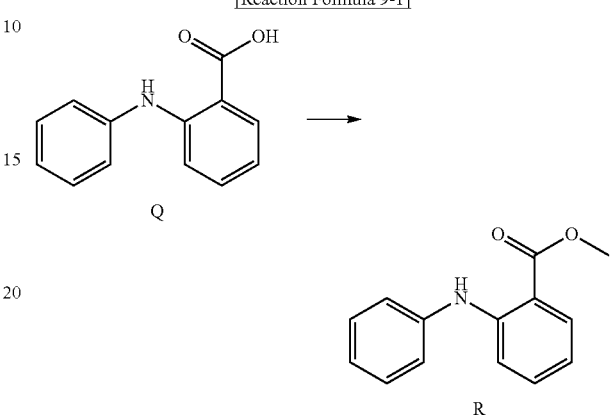

In the N₂ gas purging system, compound Q (46.9 mmol) was mixed and stirred in methanol solvent. After additionally stirring for 10 minutes under a temperature of 0° C., thionyl chloride (21.2 mmol) was slowly dropped. The mixed solution was stirred for more than 12 hours under a temperature of 90° C. After completion of the reaction, the solvent was removed, and the mixture was extracted using distilled water and ethylacetate. Moisture was removed from the extracted organic layer using magnesium sulfate. After removing residual solvent, the wet-refining process using column-chromatography with hexane and ethylacetate was performed such that compound R of deep yellow liquid was obtained.

(2) Compound S

[Reaction Formula 9-2]

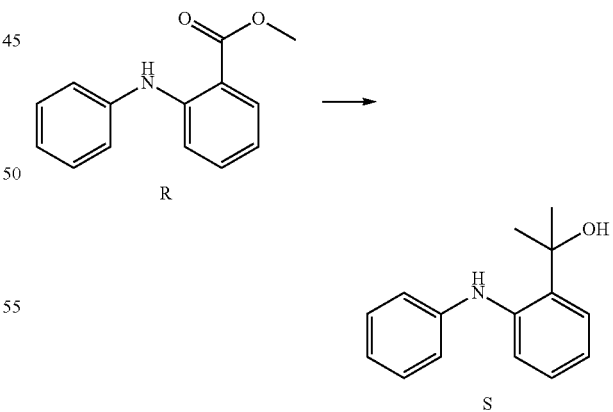

In the N₂ gas purging system, compound R (38.1 mmol) was stirred in tetrahydrofurane solvent, and methyl magnesium bromide (4.6 equivalent) was slowly dropped. The mixture was stirred for more than 13 hours under room temperature. After completion of the reaction, distilled water was slowly added, and the mixture was extracted using ethylacetate. Moisture was removed from the extracted organic layer using magnesium sulfate, and residual solvent was removed. By wet-refining using column-chromatography with hexane and ethylacetate, compound S of deep yellow liquid was obtained.

(3) Compound T

[Reaction Formula 9-3]

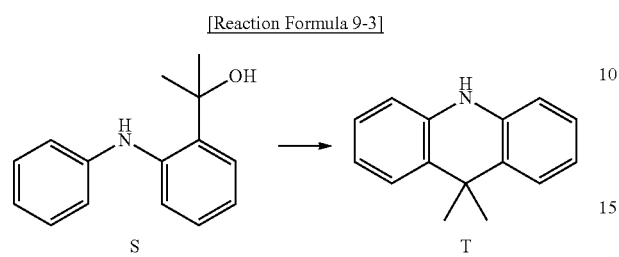

Compound S (33.1 mmol) and excess phosphoric acid solvent (160 ml) was stirred under room temperature. After stirring the mixture for more than 16 hours, distilled water (200-250 ml) was slowly added. The mixture was stirred for 0.5 to 1 hour, and the precipitated solids were filtered. The filtered solids were extracted using sodium hydroxide aqueous solution and dichloromethane solvent, and moisture was removed from the organic layer using magnesium sulfate. The residual solvent was removed such that compound T of white solid was obtained.

(4) Compound 9

[Reaction Formula 9-4]

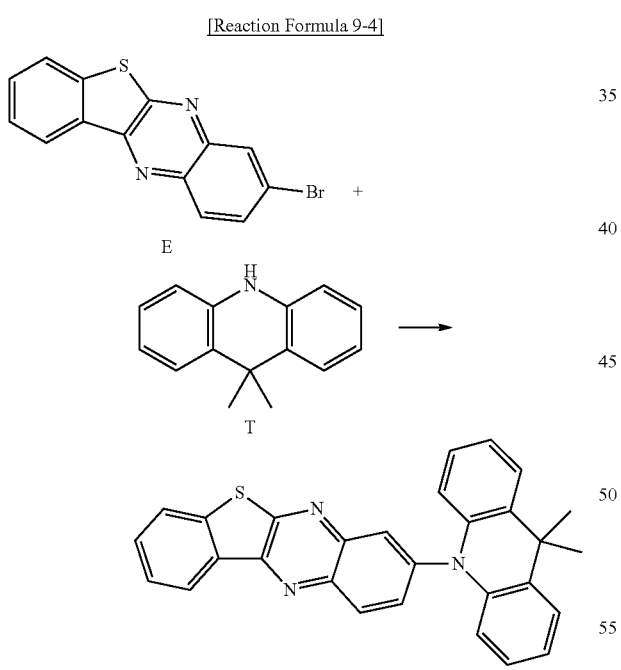

In the $N_2$ gas purging system, compound E (1.0 equivalent), compound T (1.2 equivalent), CuI (1.0 equivalent), diaminocyclohexane (3.5 equivalent), and potassium phosphate (4.0 equivalent) were put into 1,4-dioxane, and the mixture was stirred in an oil bath under a temperature of 90° C. 16 hours after, water was added into the mixture to be extracted, and the resultant was columned using the developing solvent of hexane and MC (3:1) such that compound 9 of white solid was obtained.

10. Synthesis of Compound 10

[Reaction Formula 10]

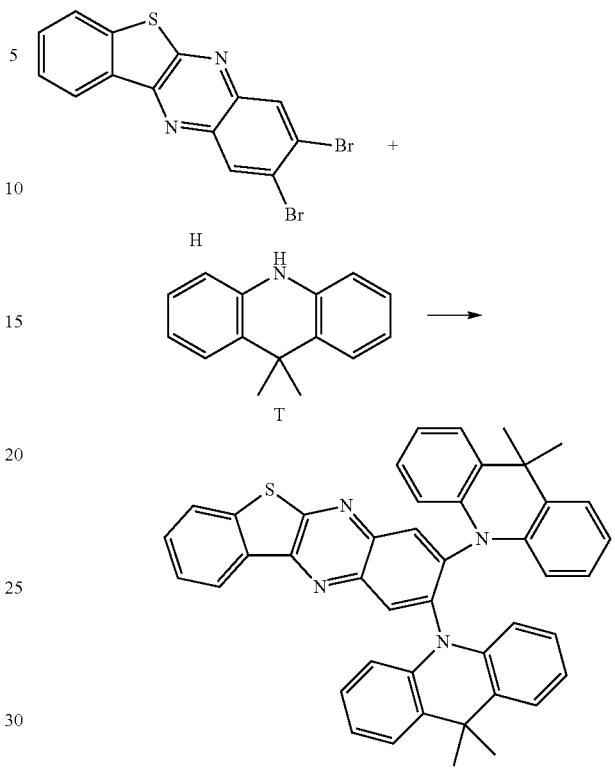

In the $N_2$ gas purging system, compound H (1.0 equivalent), compound T (2.2 equivalent), CuI (1.0 equivalent), diaminocyclohexane (3.5 equivalent), and potassium phosphate (4.0 equivalent) were put into 1,4-dioxane, and the mixture was stirred in an oil bath under a temperature of 90° C. 18 hours after, water was added into the mixture to be extracted, and the resultant was columned using the developing solvent of hexane and MC (1:1) such that compound 10 of white solid was obtained.

11. Synthesis of Compound 11

(1) Compound V

[Reaction Formula 11-1]

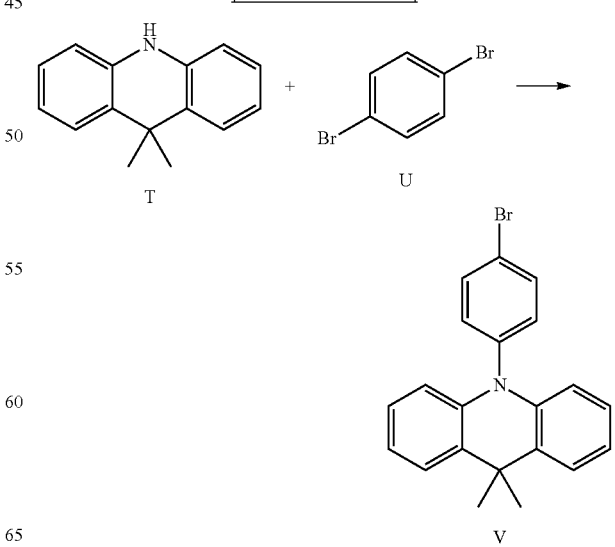

In the N₂ gas purging system, compound T (1.0 equivalent), compound U (0.8 equivalent), CuI (1.0 equivalent), diaminocyclohexane (3.5 equivalent), and potassium phosphate (4.0 equivalent) were put into 1,4-dioxane, and the mixture was stirred in an oil bath under a temperature of 90° C. 11 hours after, water was added into the mixture to be extracted, and the resultant was columned using the developing solvent of hexane and MC (9:1) such that compound V of white solid was obtained.

(2) Compound W

[Reaction Formula 11-2]

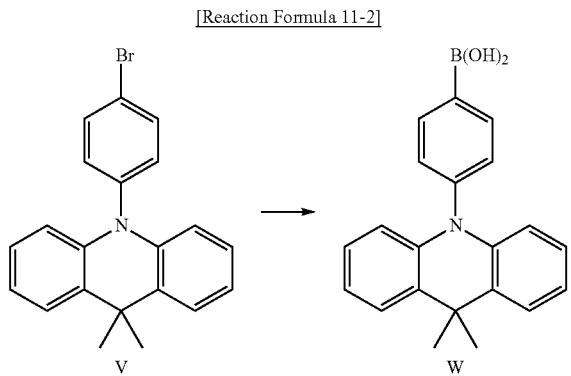

In the N₂ gas purging system, compound V (1.0 equivalent), Bu-Li (1.5 equivalent) were put into ether, and the mixture was stirred under a temperature of −78° C. After completion of the reaction for 4 hours, triethyl borate (1.2 equivalent) was added, and the mixture was stirred for 30 minutes under a temperature of −78° C. The reaction temperature was raised to room temperature by removing a dry-ice bath. After completion of the reaction for 14 hours, HCl (30 ml) diluted by DI water was added to remove the organic solvent. After completely removing the organic solvent, the white solid, which is precipitated in water, was filtered such that compound W was obtained.

(3) Compound 11

[Reaction Formula 11-3]

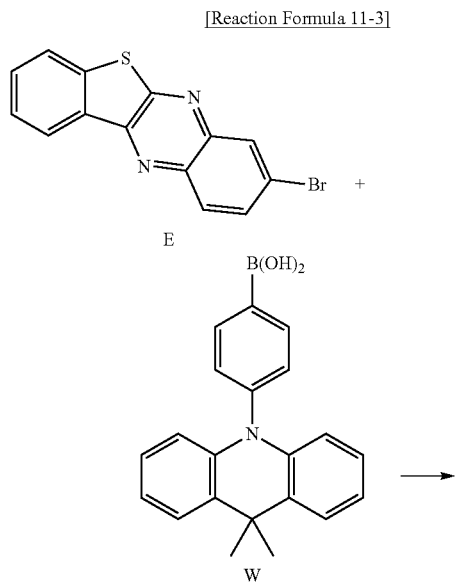

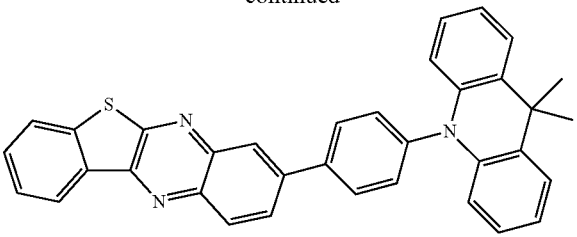

In the N₂ gas purging system, compound E (1.0 equivalent), compound W (1.3 equivalent), Pd(0) (0.05 equivalent), and potassium carbonate (4.0 equivalent) were put into toluene, and the mixture was stirred in an oil bath under a temperature of 80° C. 11 hours after, water was added into the mixture to be extracted, and the resultant was columned using the developing solvent of hexane and MC (2:1) such that compound 11 of white solid was obtained.

12. Synthesis of Compound 12

[Reaction Formula 12]

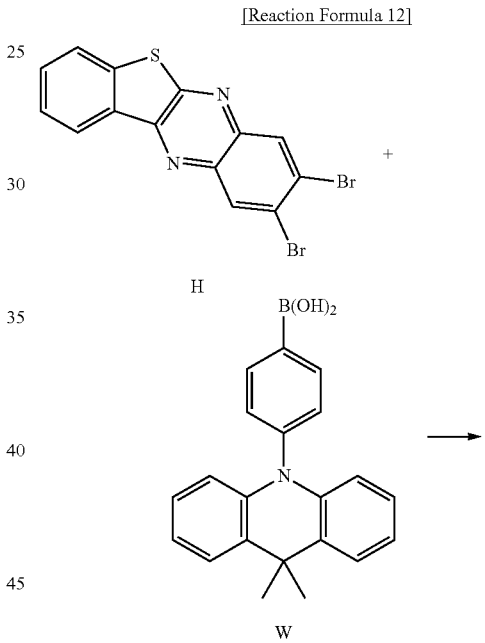

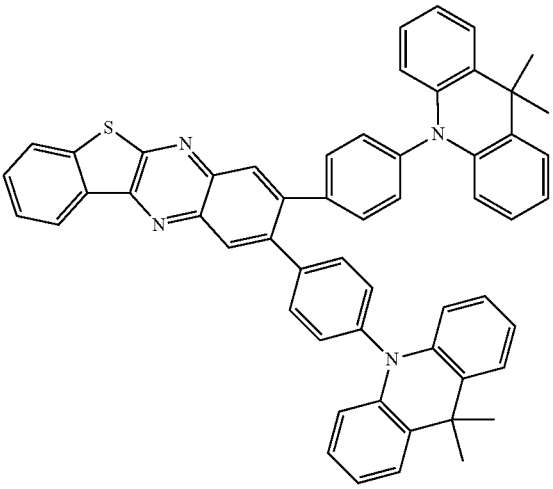

In the N₂ gas purging system, compound H (1.0 equivalent), compound W (2.3 equivalent), Pd(0) (0.05 equivalent), and potassium carbonate (4.0 equivalent) were put into toluene, and the mixture was stirred in an oil bath under a temperature of 80° C. 16 hours after, water was added into the mixture to be extracted, and the resultant was columned using the developing solvent of hexane and EA (3:1) such that compound 12 of white solid was obtained.

13. Synthesis of Compound 13

[Reaction Formula 13]

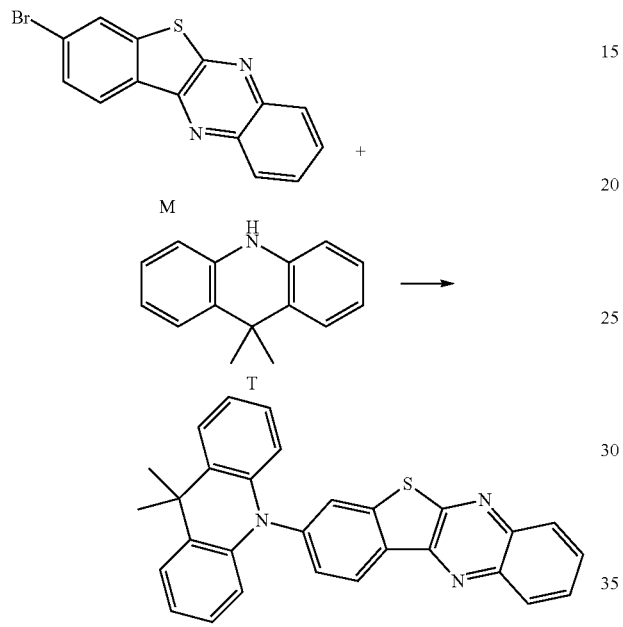

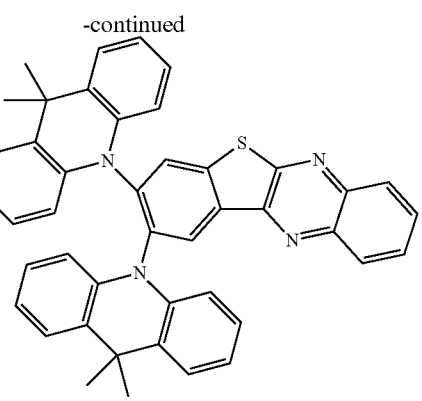

In the N₂ gas purging system, compound M (1.0 equivalent), compound T (1.2 equivalent), CuI (1.0 equivalent), diaminocyclohexane (3.5 equivalent), and potassium phosphate (4.0 equivalent) were put into 1,4-dioxane, and the mixture was stirred in an oil bath under a temperature of 90° C. 12 hours after, water was added into the mixture to be extracted, and the resultant was columned using the developing solvent of hexane and MC (4:1) such that compound 13 of white solid was obtained.

14. Synthesis of Compound 14

[Reaction Formula 14]

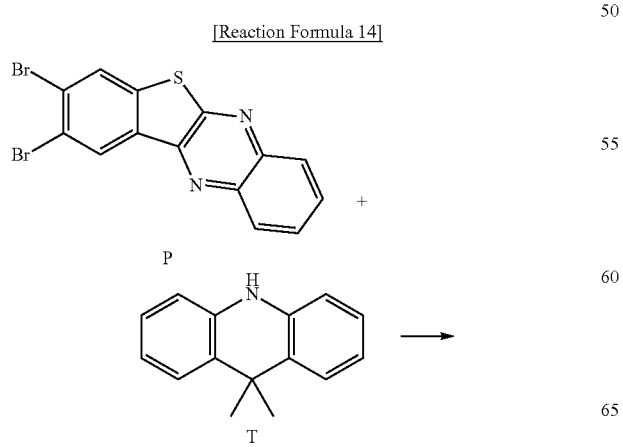

In the N₂ gas purging system, compound P (1.0 equivalent), compound T (2.3 equivalent), CuI (1.0 equivalent), diaminocyclohexane (3.5 equivalent), and potassium phosphate (4.0 equivalent) were put into 1,4-dioxane, and the mixture was stirred in an oil bath under a temperature of 90° C. 18 hours after, water was added into the mixture to be extracted, and the resultant was columned using the developing solvent of hexane and MC (1:1) such that compound 14 of white solid was obtained.

15. Synthesis of Compound 15

[Reaction Formula 15]

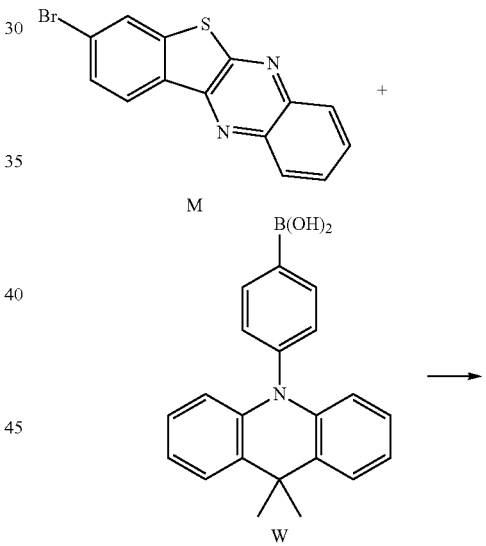

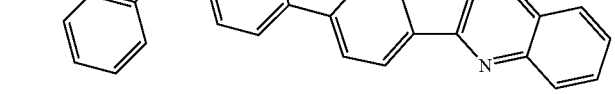

In the N₂ gas purging system, compound M (1.0 equivalent), compound W (1.3 equivalent), Pd(0) (0.05 equivalent), and potassium carbonate (4.0 equivalent) were put into toluene, and the mixture was stirred in an oil bath under a temperature of 80° C. 13 hours after, water was added into the mixture to be extracted, and the resultant was columned using the developing solvent of hexane and MC (3:1) such that compound 15 of white solid was obtained.

16. Synthesis of Compound 16

[Reaction Formula 16]

In the $N_2$ gas purging system, compound P (1.0 equivalent), compound W (2.3 equivalent), Pd(0) (0.05 equivalent), and potassium carbonate (4.0 equivalent) were put into toluene, and the mixture was stirred in an oil bath under a temperature of 80° C. 20 hours after, water was added into the mixture to be extracted, and the resultant was columned using the developing solvent of hexane and EA (3:1) such that compound 16 of white solid was obtained.

The mass spectrum data of the above compounds 1 to 16 are listed in Table 2.

TABLE 2

|  |  | Calculation | Found (M(H+)) |
|---|---|---|---|
| Com1 | $C_{26}H_{15}N_3S$ | 410.10 | 402.11 |
| Com2 | $C_{38}H_{22}N_4S$ | 566.16 | 567.29 |
| Com3 | $C_{32}H_{19}N_3S$ | 477.13 | 478.21 |
| Com4 | $C_{50}H_{30}N_4S$ | 718.22 | 719.36 |
| Com5 | $C_{26}H_{15}N_3S$ | 410.10 | 402.11 |
| Com6 | $C_{38}H_{22}N_4S$ | 566.16 | 567.29 |
| Com7 | $C_{32}H_{19}N_3S$ | 477.13 | 478.21 |
| Com8 | $C_{50}H_{30}N_4S$ | 718.22 | 719.36 |
| Com9 | $C_{29}H_{21}N_3S$ | 443.15 | 444.23 |
| Com10 | $C_{44}H_{34}N_4S$ | 650.25 | 651.21 |
| Com11 | $C_{35}H_{25}N_3S$ | 519.18 | 520.29 |
| Com12 | $C_{56}H_{42}N_4S$ | 802.31 | 803.26 |
| Com13 | $C_{29}H_{21}N_3S$ | 443.15 | 444.23 |
| Com14 | $C_{44}H_{34}N_4S$ | 650.25 | 651.21 |
| Com15 | $C_{35}H_{25}N_3S$ | 519.18 | 520.29 |
| Com16 | $C_{56}H_{42}N_4S$ | 802.31 | 803.26 |

Figure 18A:
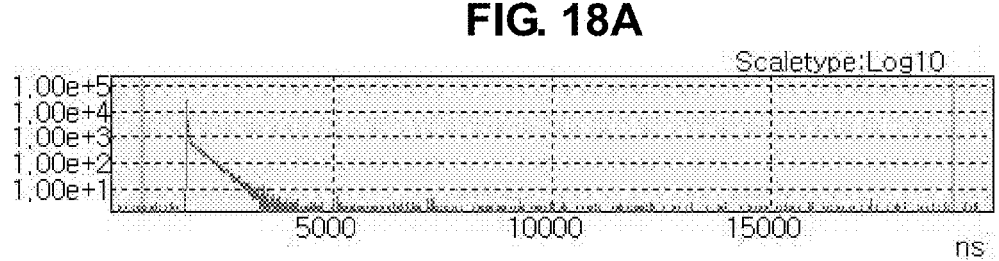
FIGS. 18A to 18C are graphs showing a delayed fluorescent property of a delayed fluorescence compound according to the present disclosure.
Figure 18B:
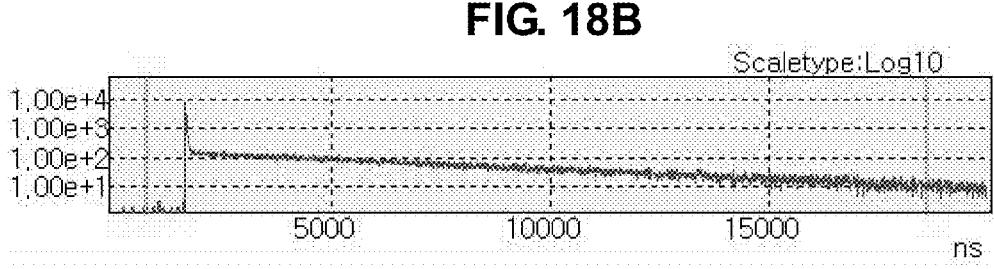
Figure 18C:
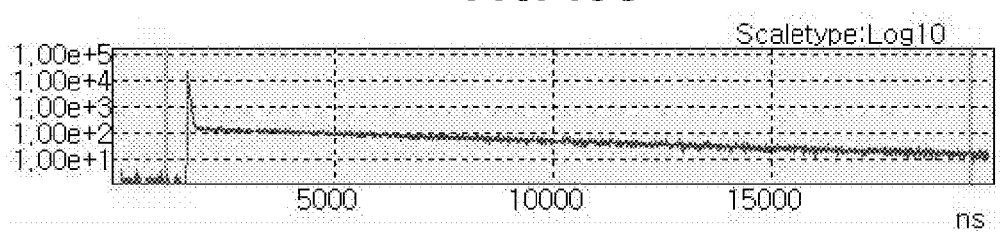

The emission properties of the reference compound (Ref) in Formula 5 and the above compounds 1 and 5 (Com1 and Com5) are measured and the results are listed in Table 3 and shown in FIGS. 18A to 18C. (Quantarus tau apparatus of Hamamatsu Co., Ltd. $O_2$ free condition)

[Formula 5]

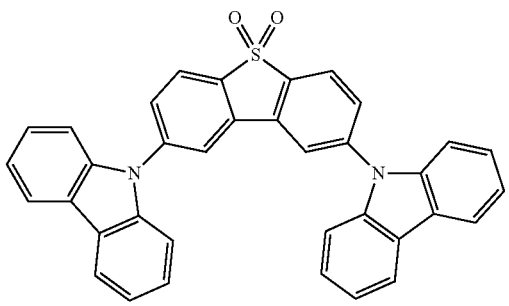

Ref

TABLE 3

|  | Prompt (ns) | Delayed (ns) |
|---|---|---|
| | 12.83 | 311.25 |

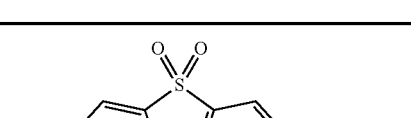

Ref

TABLE 3-continued

| | Prompt (ns) | Delayed (ns) |
|---|---|---|
| 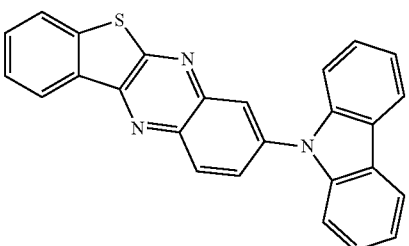 Com1 | 21.38 | 6326.62 |
| 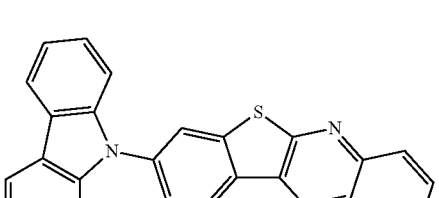 Comp5 | 26.98 | 7686.76 |

As shown in Table 3 and FIG. 18A, the reference compound (Ref) shows the delayed fluorescent emission (Delayed) of hundreds of nano-seconds. However, as shown in Table 3 and FIGS. 18B and 18C, the delayed fluorescence compounds (Com1 and Com5) of the present disclosure show the delayed fluorescent emission of hundreds of thousands of nano-seconds (ns).

As mentioned above, the delayed fluorescence compound of the present disclosure is activated by the field such that the excitons in the singlet state "$S_1$" and the triplet state "$T_1$" are transited into the intermediated state "$I_1$". As a result, both the excitons in the singlet state "$S_1$" and the excitons in the triplet state "$T_1$" are engaged in emission.

The FADF compound is a single molecule compound having the electron donor moiety and the electron acceptor moiety in the single molecule such that the charge transfer is easily generated. In the FADF compound with particular conditions, the charge can be separated from the electron donor moiety to the electron acceptor moiety.

The FADF compound is activated by outer factors. It can be verified by comparing the absorption peak and the emission peak of the solution of the compounds.

$$\Delta v = vabs - vfl = \frac{2\Delta\mu^2}{hca^3}\Delta f + \text{constant} \quad \text{(Lippert-Mataga equation)}$$

In the above equation, "$\Delta v$" is the Stock-shift value, and "$vabs$" and "$vfl$" are the wave-number of the maximum absorption peak and the maximum emission peak, respectively. "h" is Planck's constant, "c" is the velocity of light, "a" is the onsager cavity radius, and "$\Delta\mu$" is a difference between the dipole moment of the excited state and the dipole moment of the ground state. ($\Delta\mu = \mu_e - \mu_g$)

"$\Delta f$" is a value indicating the orientational polarizability of the solvent and may be a function of the dielectric constant of the solvent ($\varepsilon$) and the refractive index of the solvent (n).

$$\Delta f = \frac{\varepsilon - 1}{2\varepsilon + 1} - \frac{n^2 - 1}{2n^2 + 1}$$

Since the intensity of dipole moment in the excited state is determined by the peripheral polarity (e.g., the polarity of the solvent), the FADF can be verified by comparing the absorption peak and the emission peak of the solution of the compounds.

The orientational polarizability ($\Delta f$) of the mixed solvent can be calculated by using the orientational polarizability of each pure solvent and their mole fraction. When "$\Delta f$" and "$\Delta v$" are linearly plotted by using above "Lippert-Mataga equation", the compound may provide the FADF emission.

Namely, when the FADF complex is stabilized according to the orientational polarizability of the solvent, the emission peak is shifted in a long wavelength according to the degree of the stabilization. Accordingly, when the compound provides the FADF emission, "$\Delta f$" and "$\Delta v$" are plotted in a linear line. When "$\Delta f$" and "$\Delta v$" are plotted in a linear line, the compound provides the FADF emission.

In the delayed fluorescence compound of the present disclosure, the 25% excitons in the singlet state and the 75% excitons in the triplet state are transited into the intermediate state by an outer force, i.e., a field generated when the OLED is driven. (Intersystem crossing) The excitons in the intermediate state are transited into the ground state such that the emitting efficiency is improved. Namely, in the fluorescent compound, since the singlet exciton and the triplet exciton are both engaged in emission, the emitting efficiency is improved.

OLED

An ITO layer is deposited on a substrate and washed to form an anode (3 mm*3 mm). The substrate is loaded in a vacuum chamber, and a hole injecting layer (40 Å, NPB(N, N'-di(naphthalen-1-yl)-N,N'-diphenyl-benzidine)), a hole transporting layer (10 Å, mCP(N,N'-Dicarbazolyl-3,5-benzene)), an emitting material layer (200 Å, host (bis{2-[di(phenyl)phosphino]phenyl}ether oxide) and dopant (12%)), an electron transporting layer (300 Å, 1,3,5-tri(phenyl-2-benzimidazole)-benzene), an electron injecting layer (10 Å, LiF), and a cathode (Al) are sequentially formed on the anode under a base pressure of about $10^{-6}$ to $10^{-7}$ Torr.

(1) Example 1 (Ex1)

The compound 1 is used as the dopant to form the OLED.

(2) Example 2 (Ex2)

The compound 2 is used as the dopant to form the OLED.

(3) Example 3 (Ex3)

The compound 5 is used as the dopant to form the OLED.

(4) Example 4 (Ex4)

The compound 6 is used as the dopant to form the OLED.

(5) Example 5 (Ex5)

The compound 9 is used as the dopant to form the OLED.

(6) Example 6 (Ex6)

The compound 10 is used as the dopant to form the OLED.

(7) Example 7 (Ex7)

The compound 13 is used as the dopant to form the OLED.

(8) Example 8 (Ex8)

The compound 14 is used as the dopant to form the OLED.

(9) Comparative Example (Ref)

The reference compound in Formula 5 is used as the dopant to form the OLED.

TABLE 4

| | Voltage | Efficiency | | EQE | | |
|---|---|---|---|---|---|---|
| | (V) | cd/A | lm/W | (%) | CIE(X) | CIE(Y) |
| Ex1 | 4.6 | 6.7 | 4.57 | 6.9 | 0.154 | 0.098 |
| Ex2 | 4.7 | 7.4 | 4.94 | 8.0 | 0.147 | 0.083 |
| Ex3 | 4.4 | 7.5 | 5.4 | 8.3 | 0.150 | 0.134 |
| Ex4 | 4.4 | 8.4 | 6.0 | 9.2 | 0.151 | 0.099 |
| Ex5 | 4.2 | 8.9 | 6.7 | 9.4 | 0.152 | 0.153 |
| Ex6 | 4.0 | 9.3 | 7.3 | 10.2 | 0.161 | 0.158 |
| Ex7 | 4.3 | 8.6 | 6.3 | 9.1 | 0.150 | 0.142 |

TABLE 4-continued

| | Voltage | Efficiency | | EQE | | |
|---|---|---|---|---|---|---|
| | (V) | cd/A | lm/W | (%) | CIE(X) | CIE(Y) |
| Ex8 | 4.2 | 9.8 | 7.3 | 10.4 | 0.158 | 0.160 |
| Ref | 6.72 | 1.61 | 0.75 | 2.64 | 0.158 | 0.141 |

As shown in Table 4, in the OLEDs using the compounds of the present disclosure (Ex1 to Ex8), the color purity and the emitting efficiency are improved. Namely, in the compound including carbazole as the electron donor moiety, the property of the compound is strongly changed according to the electron acceptor moiety. In the delayed compound of the present disclosure including benzo[4,5]thieno[2,3-b]quinoxaline as the electron acceptor moiety, with the strong electron accepting property, the color purity is improved. In addition, in the delayed compound of the present disclosure, the triplet excitons are engaged in the emission such that the emitting efficiency is strongly improved.

Figure 19:
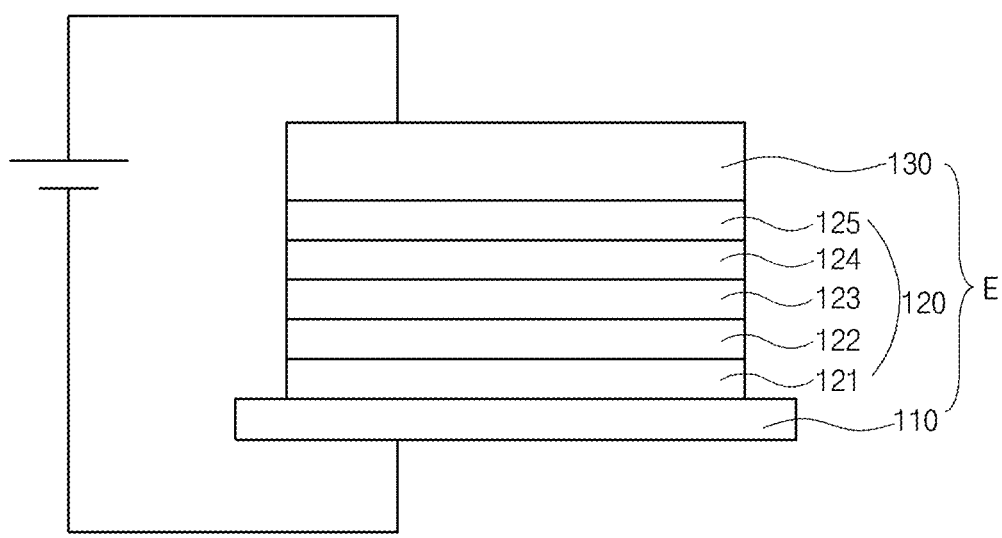
FIG. 19 is a schematic cross-sectional view of an OLED according to the disclosure.

FIG. 19 is a schematic cross-sectional view of an OLED according to the invention.

As shown in FIG. 19, the OLED "E" is formed on a substrate (not shown). The OLED "E" includes a first electrode 110 as an anode, a second electrode 130 as a cathode, and an organic emitting layer 120 therebetween.

Although not shown, an encapsulation film, which includes at least one inorganic layer and at least one organic layer and covers the OLED "E", and a cover window on the encapsulation film may be further formed to form a display device including the OLED "E". The substrate, the encapsulation film, and the cover window may have a flexible property such that a flexible display device may be provided.

The first electrode 110 is formed of a material having a relatively high work function, and the second electrode 130 is formed of a material having a relatively low work function. For example, the first electrode 110 may be formed of indium-tin-oxide (ITO), and the second electrode 130 may be formed of aluminum (Al) or Al alloy (AlNd). The organic emitting layer 120 may include red, green, and blue emitting patterns.

The organic emitting layer 120 may have a single-layered structure. Alternatively, to improve the emitting efficiency, the organic emitting layer 120 includes a hole injection layer (HIL) 121, a hole transporting layer (HTL) 122, an emitting material layer (EML) 123, an electron transporting layer (ETL) 124, and an electron injection layer (EIL) 125 sequentially stacked on the first electrode 110.

At least one of the HIL 121, the HTL 122, the EML 123, the ETL 124, and the EIL 125 includes the delayed fluorescence compound in the Formula 1.

For example, the EML 123 may include the delayed fluorescence compound in the Formula 1. The delayed fluorescence compound acts as the dopant, and the EML 123 may further include a host to emit blue light. In this instance, the dopant has about 1 to 30 weight % with respect to the host.

A difference between the HOMO of the host "$HOMO_{Host}$" and the HOMO of the dopant "$HOMO_{Dopant}$" or a difference between the LUMO of the host "$LUMO_{Host}$" and the LUMO of the dopant "$LUMO_{Dopant}$" is less than 0.5 eV. ($|HOMO_{Host}-HOMO_{Dopant}| \leq 0.5$ eV or $|LUMO_{Host}-LUMO_{Dopant}| \leq 0.5$ eV) In this instance, the charge transfer efficiency from the host to the dopant may be improved.

For example, the host, which meets the above condition, may be selected from materials in Formula 6. (Bis[2-

(diphenylphosphino)phenyl]ether oxide (DPEPO), 2,8-bis(diphenylphosphoryl)dibenzothiophene (PPT), 2,8-di(9H-carbazol-9-yl)dibenzothiophene (DCzDBT), m-bis(carbazol-9-yl)biphenyl (m-CBP), Diphenyl-4-triphenylsilylphenyl-phosphine oxide (TPSOI), 9-(9-phenyl-9H-carbazol-6-yl)-9H-carbazole (CCP) in order.)

[Formula 6]

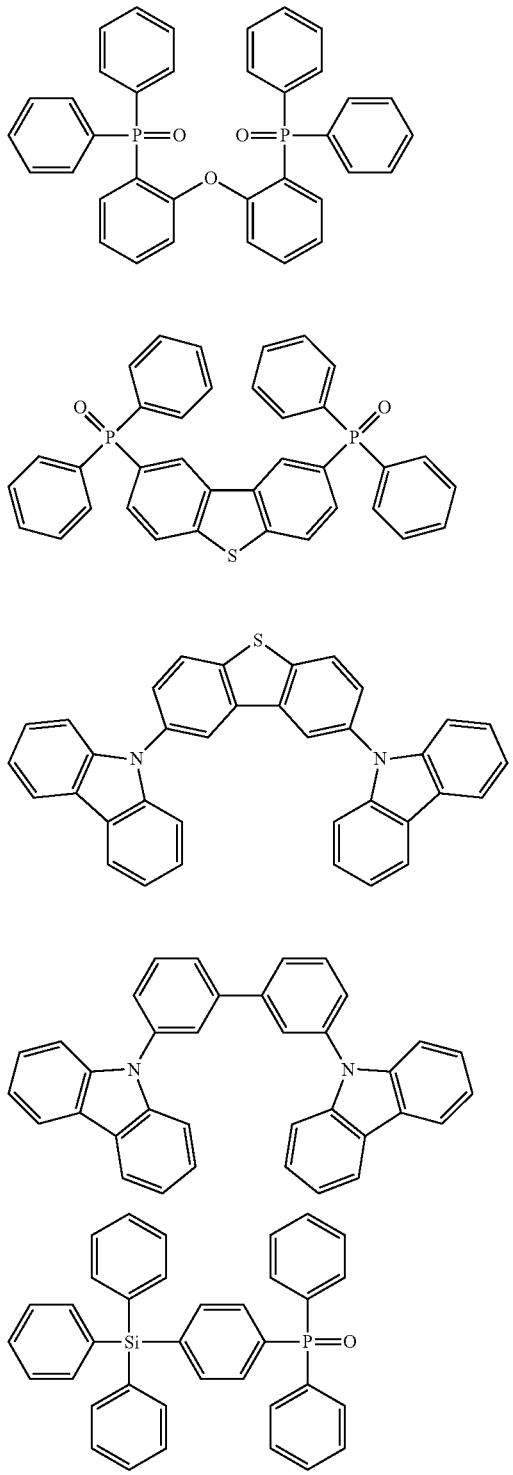

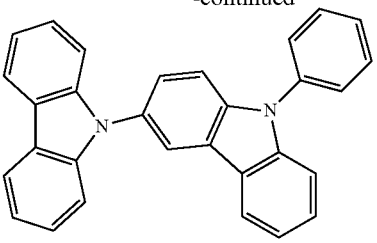

The triplet energy of the dopant is smaller than the triplet energy of the host, and a difference between the singlet energy of the dopant and the triplet energy of the dopant is less than 0.3 eV. (ΔEST≤0.3 eV) As the difference "ΔEST" is smaller, the emitting efficiency is higher. In the delayed fluorescence compound of the present invention, even if the difference "ΔEST" between the singlet energy of the dopant and the triplet energy of the dopant is about 0.3 eV, which is relatively large, the excitons in the singlet state "S1" and the excitons in the triplet state "T1" can be transited into the intermediate state "I1".

On the other hand, the delayed fluorescence compound of the present disclosure may act as a host in the EML 123, and the EML 123 may further include a dopant to emit the blue light. In this instance, the dopant has about 1 to 30 weight % with respect to the host. Since the development of the blue host having excellent properties is insufficient, the delayed fluorescence compound of the present disclosure may be used as the host to increase the degree of freedom for the host. In this instance, the triplet energy of the dopant may be smaller than the triplet energy of the host of the delayed fluorescence compound of the present disclosure.

The EML 123 may include a first dopant of the delayed fluorescence compound of the present disclosure, a host, and a second dopant. The weight % summation of the first and second dopants may be about 1 to 30 to emit blue light. In this instance, the emitting efficiency and the color purity may be further improved.

In this instance, the triplet energy of the first dopant, i.e., the delayed fluorescence compound of the present disclosure, may be smaller than the triplet energy of the host and larger than the triplet energy of the second dopant. In addition, a difference between the singlet energy of the first dopant and the triplet energy of the first dopant is less than 0.3 eV. ($\Delta E_{ST}$<0.3 eV) As the difference "$\Delta E_{ST}$" is smaller, the emitting efficiency is higher. In the delayed fluorescence compound of the present disclosure, even if the difference "$\Delta E_{ST}$" between the singlet energy of the dopant and the triplet energy of the dopant is about 0.3 eV, which is relatively large, the excitons in the singlet state "$S_1$" and the excitons in the triplet state "$T_1$" can be transited into the intermediate state "$I_1$".

As mentioned above, in the delayed fluorescence compound of the present disclosure, since the electron donor moiety and the electron acceptor moiety are combined or covalently bonded or linked in one molecule and benzo[4,5]thieno[2,3-b]quinoxaline as the electron acceptor moiety has a strong electron accepting property and the electron donor moiety is combined or covalently bonded to the electron acceptor moiety, the emitting efficiency of the compound is improved. Namely, the dipole is formed from the electron donor moiety to the electron acceptor moiety such that the dipole moment inside the molecule is increased. As a result, the emitting efficiency is improved. In addition, the excitons in the triplet state are engaged in the emission such that the emitting efficiency of the compound is strongly improved.

In addition, the dihedral angle between the electron acceptor moiety and the electron donor moiety is increased such that the compound provides deep blue light.

Accordingly, the OLED using the delayed fluorescence compound of the present disclosure has advantages in emitting efficiency and image quality.

It will be apparent to those skilled in the art that various modifications and variations can be made in the embodiment of the invention without departing from the spirit or scope of the invention. Thus, it is intended that the embodiment of the invention cover the modifications and variations of this invention provided they come within the scope of the appended claims and their equivalents.

What is claimed is:

1. A delayed fluorescence compound, comprising:
    an electron acceptor moiety of benzo[4,5]thieno[2,3-b]quinoxaline; and
    at least one electron donor moiety covalently bonded to a benzene ring of benzo[4,5]thieno[2,3-b]quinoxaline and selected from the group consisting of carbazole, phenylcarbazole, acridine, substituted acridine, phenylacridine, and substituted phenylacridine.

2. The delayed fluorescence compound according to claim 1, wherein the delayed fluorescence compound is expressed by Formula 1:

[Formula 1]

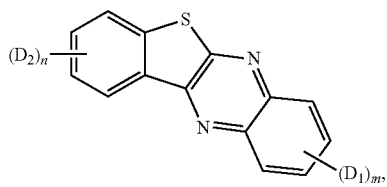

wherein the at least one electron donor moiety corresponds to $(D_1)_m$, and $(D_2)_n$, wherein each of m and n is an integer of 0 (zero) to 2, and one of m and n is 0, and each of $D_1$ and $D_2$ is independently selected from Formula 2:

[Formula 2]

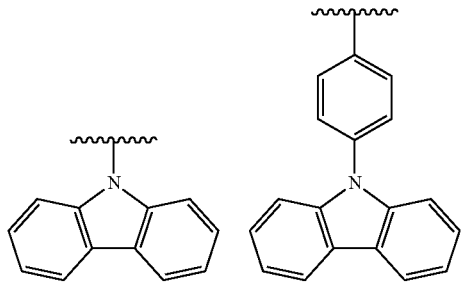

-continued

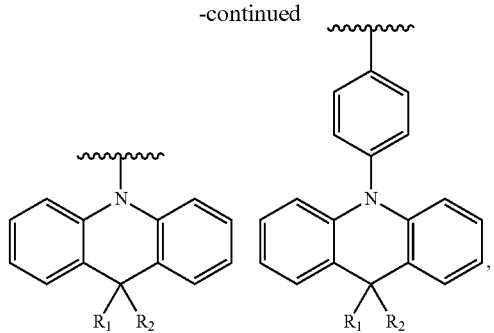

and
    wherein each of "$R_1$" and "$R_2$" is independently selected from C1~C10 alkyl.

3. The delayed fluorescence compound according to claim 2, wherein a difference between a singlet energy of the delayed fluorescence compound and a triplet energy of the delayed fluorescence compound is less than 0.3 eV.

4. An organic light emitting diode, comprising:
    a first electrode;
    a second electrode facing the first electrode; and
    an organic emitting layer between the first electrode and the second electrode, the organic emitting layer including a delayed fluorescence compound,
    wherein the delayed fluorescence compound includes an electron acceptor moiety of benzo[4,5]thieno[2,3-b]quinoxaline and an electron donor moiety covalently bonded to a benzene ring of benzo[4,5]thieno[2,3-b]quinoxaline, the electron donor moiety selected from the group consisting of carbazole, phenylcarbazole, acridine, substituted acridine, phenylacridine, and substituted phenylacridine.

5. The organic light emitting diode according to claim 4, wherein the organic emitting layer includes a hole injection layer (HIL), a hole transporting layer (HTL), an emitting material layer (EML), an electron transporting layer (ETL), and an electron injection layer (EIL), and wherein at least one of the HIL, the HTL, the EML, the ETL, and the EIL includes the delayed fluorescence compound.

6. The organic light emitting diode according to claim 4, wherein a difference between a singlet energy of the delayed fluorescence compound and a triplet energy of the delayed fluorescence compound is less than 0.3 eV.

7. The organic light emitting diode according to claim 4, wherein the organic emitting layer further includes a host, and the delayed fluorescence compound is used as a dopant.

8. The organic light emitting diode according to claim 7, wherein a difference between a highest occupied molecular orbital (HOMO) of the host and a HOMO of the dopant or a difference between a lowest unoccupied molecular orbital (LUMO) of the host and a LUMO of the dopant is less than 0.5 eV.

9. The organic light emitting diode according to claim 4, wherein the organic emitting layer further includes a dopant, and the delayed fluorescence compound is used as a host.

10. The organic light emitting diode according to claim 4, wherein the organic emitting layer further includes a host and a first dopant, and the delayed fluorescence compound is used as a second dopant, and wherein a triplet energy of the second dopant is smaller than a triplet energy of the host and larger than a triplet energy of the first dopant.

11. The organic light emitting diode according to claim 4, wherein the delayed fluorescence compound is expressed by Formula 1:

[Formula 1]

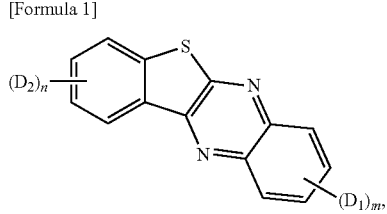

wherein the at least one electron donor moiety corresponds to $(D1)_m$ and $(D2)_n$,
wherein each of m and n is an integer of 0 (zero) to 2, and one of m and n is 0, and each of $D_1$ and $D_2$ is independently selected from Formula 2:

[Formula 2]

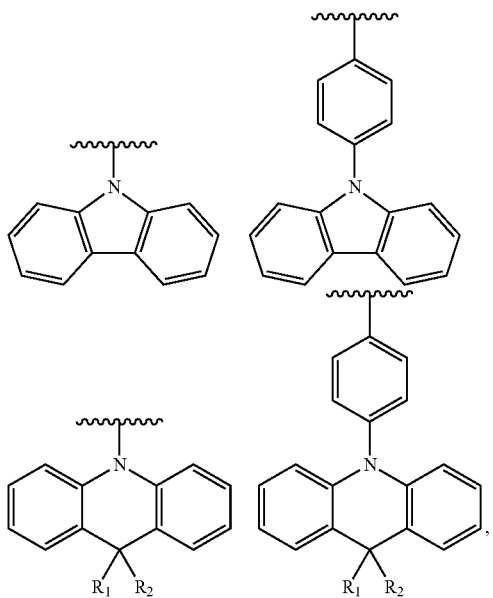

and
wherein each of "$R_1$" and "$R_2$" is independently selected from C1~C10 alkyl.

12. A display device, comprising:
a substrate;
an organic light emitting diode on the substrate and including a first electrode, a second electrode facing the first electrode, and an organic emitting layer between the first electrode and the second electrode, the organic emitting layer including a delayed fluorescence compound;
an encapsulation film on the organic light emitting diode; and
a cover window on the encapsulation film,
wherein the delayed fluorescence compound includes an electron acceptor moiety of benzo[4,5]thieno[2,3-b]quinoxaline and an electron donor moiety covalently bonded to a benzene ring of benzo[4,5]thieno[2,3-b]quinoxaline, the electron donor moiety selected from the group consisting of carbazole, phenylcarbazole, acridine, substituted acridine, phenylacridine, and substituted phenylacridine.

13. The display device according to claim 12, wherein the delayed fluorescence compound is expressed by Formula 1:

[Formula 1]

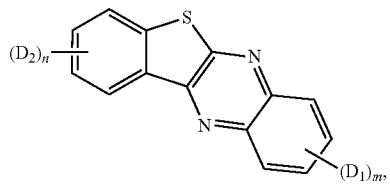

wherein the at least one electron donor moiety corresponds to $(D1)_m$ and $(D2)_n$,
wherein each of m and n is an integer of 0 (zero) to 2, and one of m and n is 0, and each of $D_1$ and $D_2$ is independently selected from Formula 2:

[Formula 2]

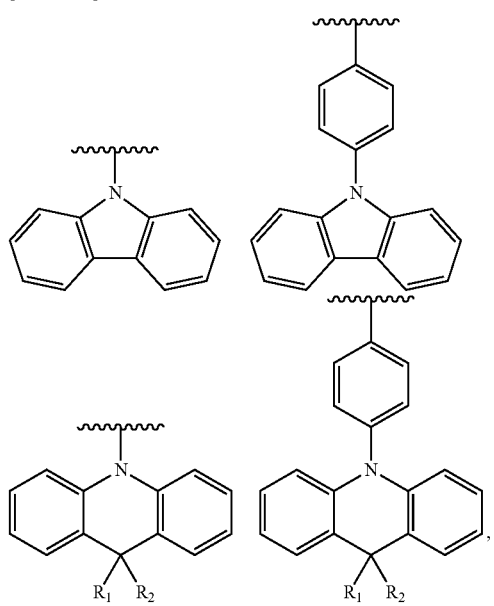

and
wherein each of "$R_1$" and "$R_2$" is independently selected from C1~C10 alkyl.

14. The display device according to claim 12, wherein the organic emitting layer includes a hole injection layer (HIL), a hole transporting layer (HTL), an emitting material layer (EML), an electron transporting layer (ETL), and an electron injection layer (EIL), and wherein at least one of the HIL, the HTL, the EML, the ETL, and the EIL includes the delayed fluorescence compound.

15. The display device according to claim 12, wherein a difference between a singlet energy of the delayed fluorescence compound and a triplet energy of the delayed fluorescence compound is less than 0.3 eV.

16. The display device according to claim 12, wherein the organic emitting layer further includes a host, and the delayed fluorescence compound is used as a dopant.

17. The display device according to claim 16, wherein a difference between a highest occupied molecular orbital (HOMO) of the host and a HOMO of the dopant or a difference between a lowest unoccupied molecular orbital (LUMO) of the host and a LUMO of the dopant is less than 0.5 eV.

18. The display device according to claim 12, wherein the organic emitting layer further includes a dopant, and the delayed fluorescence compound is used as a host.

19. The display device according to claim 12, wherein the organic emitting layer further includes a host and a first dopant, and the delayed fluorescence compound is used as a second dopant, and wherein a triplet energy of the second dopant is smaller than a triplet energy of the host and larger than a triplet energy of the first dopant.

* * * * *